United States Patent
Crawford et al.

(10) Patent No.: US 12,246,119 B2
(45) Date of Patent: Mar. 11, 2025

(54) PATIENT LINE BLOCKAGE DETECTION

(71) Applicant: Fresenius Medical Care Holdings, Inc., Waltham, MA (US)

(72) Inventors: William Scott Crawford, Palo Alto, CA (US); Robert Matthew Ohline, Redwood City, CA (US)

(73) Assignee: Fresenius Medical Care Holdings, Inc., Waltham, MA (US)

( * ) Notice: Subject to any disclaimer, the term of this patent is extended or adjusted under 35 U.S.C. 154(b) by 0 days.

(21) Appl. No.: 18/144,729

(22) Filed: May 8, 2023

(65) Prior Publication Data
US 2023/0270922 A1  Aug. 31, 2023

Related U.S. Application Data

(63) Continuation of application No. 17/369,372, filed on Jul. 7, 2021, now Pat. No. 11,679,184, which is a
(Continued)

(51) Int. Cl.
*A61M 1/14* (2006.01)
*A61M 1/28* (2006.01)
(Continued)

(52) U.S. Cl.
CPC .............. *A61M 1/14* (2013.01); *A61M 1/154* (2022.05); *A61M 1/155* (2022.05); *A61M 1/159* (2022.05);
(Continued)

(58) Field of Classification Search
CPC ........ A61M 1/14; A61M 1/154; A61M 1/155; A61M 1/159; A61M 1/28; A61M 1/285;
(Continued)

(56) References Cited

U.S. PATENT DOCUMENTS

| 5,438,510 A | 8/1995 | Bryant et al. |
| 8,021,334 B2 | 9/2011 | Shekalim |

(Continued)

FOREIGN PATENT DOCUMENTS

| CN | 102196833 | 9/2011 |
| EP | 2158930 | 3/2010 |

(Continued)

OTHER PUBLICATIONS

International Preliminary Report on Patentability in International Application No. PCT/US2017/037167, dated Jan. 1, 2019, 11 pages.
(Continued)

*Primary Examiner* — Shefali D Patel
(74) *Attorney, Agent, or Firm* — Fish & Richardson P.C.

(57) ABSTRACT

A dialysis machine (e.g., a peritoneal dialysis (PD) machine) can include a pressure sensor mounted at a proximal end of a patient line made of a distensible material that provides PD solution to a patient through a catheter. During treatment, an occlusion can occur at different locations in the patient line and/or the catheter. When an incremental volume of additional solution is provided to the patient line while the occlusion is present, a change in pressure results. The change in pressure depends on dimensions and a distensibility of a non-occluded portion of the patient line. If the change in pressure, the incremental volume, properties related to the distensibility of the patient line, and some of the dimensions of the patient line are known, a location of the occlusion can be inferred. An occlusion type can be inferred based on the inferred location.

20 Claims, 23 Drawing Sheets

Related U.S. Application Data continuation of application No. 15/198,211, filed on Jun. 30, 2016, now Pat. No. 11,071,809.

(51) Int. Cl.
*A61M 1/36* (2006.01)
*A61M 5/168* (2006.01)

(52) U.S. Cl.
CPC .............. *A61M 1/28* (2013.01); *A61M 1/285* (2013.01); *A61M 1/3656* (2014.02); *A61M 5/16831* (2013.01); *A61M 5/16854* (2013.01); *A61M 1/1522* (2022.05); *A61M 1/1524* (2022.05); *A61M 1/1561* (2022.05); *A61M 1/1565* (2022.05); *A61M 1/3661* (2014.02); *A61M 2005/16863* (2013.01); *A61M 2005/16868* (2013.01); *A61M 2205/18* (2013.01); *A61M 2205/3331* (2013.01); *A61M 2205/3355* (2013.01); *A61M 2205/3362* (2013.01); *A61M 2205/50* (2013.01); *A61M 2205/52* (2013.01); *A61M 2205/70* (2013.01); *A61M 2205/702* (2013.01); *A61M 2209/02* (2013.01); *A61M 2210/1017* (2013.01)

(58) Field of Classification Search
CPC .......... A61M 1/36224; A61M 1/36225; A61M 1/3656; A61M 1/3659; A61M 1/3661; A61M 1/3663; A61M 1/73; A61M 1/732; A61M 1/734; A61M 1/77; A61M 1/80; A61M 2005/16863; A61M 2005/16868; A61M 2005/16872; A61M 2205/0216; A61M 2205/33; A61M 2205/3327; A61M 2205/3331; A61M 2205/3334; A61M 2205/3362; A61M 2205/3379; A61M 2205/50; A61M 2210/1017; A61M 5/14; A61M 5/142; A61M 5/168; A61M 5/16831; A61M 5/16854; A61M 5/16886; A61M 5/172; A61M 5/48; A61M 5/486
See application file for complete search history.

(56) References Cited

U.S. PATENT DOCUMENTS

| | | |
|---|---|---|
| 8,167,832 B2 | 5/2012 | Bowman et al. |
| 8,317,770 B2 | 11/2012 | Miesel et al. |
| 8,556,225 B2 | 10/2013 | Gray |
| 2007/0270782 A1 | 11/2007 | Miesel et al. |
| 2008/0139996 A1 | 6/2008 | Bowman et al. |
| 2008/0262406 A1 | 10/2008 | Wiener |
| 2012/0186509 A1 | 7/2012 | Milijasevic et al. |
| 2013/0014593 A1 | 1/2013 | Tabaru et al. |
| 2018/0236165 A1 | 8/2018 | Dearmond et al. |

FOREIGN PATENT DOCUMENTS

| | | |
|---|---|---|
| JP | 2013-024574 | 2/2013 |
| WO | WO 2007/123764 | 11/2007 |
| WO | WO 2015/029039 | 3/2015 |

OTHER PUBLICATIONS

International Search Report and Written Opinion in International Application No. PCT/US2017/037167, dated Sep. 6, 2017, 26 pages (with English translation).

PATIENT LINE BLOCKAGE DETECTION

CROSS-REFERENCE TO RELATED APPLICATIONS

This application is a continuation of U.S. application Ser. No. 17/369,372, filed on Jul. 7, 2021, which is a continuation of U.S. application Ser. No. 15/198,211, filed Jun. 30, 2016. The disclosure of the prior applications is considered part of (and is incorporated by reference in) the disclosure of this application.

TECHNICAL FIELD

This disclosure relates to detecting a blockage in a patient line.

BACKGROUND

Dialysis is a treatment used to support a patient with insufficient renal function. The two principal dialysis methods are hemodialysis and peritoneal dialysis. During hemodialysis ("HD"), the patient's blood is passed through a dialyzer of a dialysis machine while also passing a dialysis solution or dialysate through the dialyzer. A semi-permeable membrane in the dialyzer separates the blood from the dialysate within the dialyzer and allows diffusion and osmosis exchanges to take place between the dialysate and the blood stream. These exchanges across the membrane result in the removal of waste products, including solutes like urea and creatinine, from the blood. These exchanges also regulate the levels of other substances, such as sodium and water, in the blood. In this way, the dialysis machine acts as an artificial kidney for cleansing the blood.

During peritoneal dialysis ("PD"), the patient's peritoneal cavity is periodically infused with dialysate. The membranous lining of the patient's peritoneum acts as a natural semi-permeable membrane that allows diffusion and osmosis exchanges to take place between the solution and the blood stream. These exchanges across the patient's peritoneum result in the removal of waste products, including solutes like urea and creatinine, from the blood, and regulate the levels of other substances, such as sodium and water, in the blood.

Automated PD machines called PD cyclers are designed to control the entire PD process so that it can be performed at home usually overnight without clinical staff in attendance. This process is termed continuous cycler-assisted PD (CCPD). Many PD cyclers are designed to automatically infuse, dwell, and drain dialysate to and from the patient's peritoneal cavity. The treatment typically lasts for several hours, often beginning with an initial drain cycle to empty the peritoneal cavity of used or spent dialysate. The sequence then proceeds through the succession of fill, dwell, and drain phases that follow one after the other. Each phase is called a cycle.

SUMMARY

In one aspect, a method includes measuring a first pressure of fluid in a first portion of a distensible medical tube connected to a medical device. An occlusion is present in the medical tube at a location that defines a boundary between the first portion and a second portion of the medical tube. The method also includes providing or withdrawing a volume of fluid to or from the first portion of the medical tube. The method also includes measuring a second pressure of the fluid in the first portion of the medical tube. The method also includes determining a length of the first portion of the medical tube based on a difference between the second pressure and the first pressure.

Implementations can include one or more of the following features.

In some implementations, the medical device includes a dialysis machine.

In some implementations, the dialysis machine includes a peritoneal dialysis (PD) machine.

In some implementations, the length of the first portion represents the location of the occlusion relative to a proximal end of the medical tube connected to the medical device.

In some implementations, the first pressure and the second pressure are measured by a pressure sensor at a proximal end of the medical tube connected to the medical device.

In some implementations, the fluid is at least partially blocked by the occlusion.

In some implementations, the fluid being at least partially blocked by the occlusion causes an increase or a decrease in pressure in the medical tube.

In some implementations, the fluid being at least partially blocked by the occlusion causes a distension in the medical tube.

In some implementations, the medical tube includes a catheter at a distal end of the medical tube.

In some implementations, the method includes inferring a type of the occlusion based at least in part on a determined location of the occlusion.

In some implementations, the type of the occlusion includes one or more of a pinch of the medical tube, a kink in the medical tube, a deposit in the medical tube, and a deposit blocking a hole of a catheter at a distal end of the medical tube.

In some implementations, the deposit includes omental fat.

In some implementations, the method includes determining the length of the first portion of the medical tube based on one or more of dimensions of the medical tube, a material composition of the medical tube, and the volume of fluid provided to or withdrawn from the first portion of the medical tube.

In some implementations, the determination of the length of the first portion of the medical tube is based on a fluidic capacitance of the medical tube.

In some implementations, the method includes measuring a time history of pressures of the fluid in the first portion of the medical tube.

In some implementations, the method includes measuring two pressures of the fluid in the first portion of the medical tube while the volume of fluid is being provided or withdrawn. The method also includes determining the length of the first portion of the medical tube based on a difference between the two pressure measurements and an amount of time elapsed between the two pressure measurements.

In some implementations, the method includes measuring a third pressure of the fluid in the first portion of the medical tube before the providing or withdrawing of the volume of fluid is abruptly stopped. The method also includes measuring a plurality of pressures over time of the fluid in the first portion of the medical tube after the providing or withdrawing of the volume of fluid is abruptly stopped. The method also includes determining the length of the first portion of the medical tube based on an elapsed time between the third pressure measurement and a fourth pressure measurement of the plurality of pressure measurements over time.

In another aspect, a method includes providing or withdrawing a fluid to or from a distensible medical tube connected to a medical device at a volumetric flow rate over time. The medical tube includes a patient line region and a catheter region separated by a fluid capacitive element. The method also includes measuring, by a pressure sensor at the patient line region, a plurality of pressures over time of the fluid. The method also includes determining whether an occlusion in the medical tube is present in the patient line region or the catheter region based on the measured pressures over time.

Implementations can include one or more of the following features.

In some implementations, the medical device includes a dialysis machine.

In some implementations, the dialysis machine includes a PD machine.

In some implementations, the volumetric flow rate over time includes a dispensing or withdrawing step of fluid that is abruptly stopped.

In some implementations, the volumetric flow rate over time includes one or more of a steady-state introduction of fluid, a ramped introduction of fluid, a parabolic introduction of fluid, and a cyclical introduction of fluid.

In some implementations, the fluid is at least partially blocked by the occlusion.

In some implementations, the fluid being at least partially blocked by the occlusion causes an increase or a decrease in pressure in the medical tube.

In some implementations, the fluid being at least partially blocked by the occlusion causes a distension in the medical tube.

In some implementations, the medical tube includes a catheter in the catheter region at a distal end of the medical tube.

In some implementations, the method includes inferring a type of the occlusion based at least in part on a determined location of the occlusion.

In some implementations, the type of the occlusion includes one or more of a pinch of the medical tube, a kink in the medical tube, a deposit in the medical tube, and a deposit blocking a hole of a catheter in the catheter region at a distal end of the medical tube.

In some implementations, the method includes determining whether the occlusion in the medical tube is present in the patient line region or the catheter region based on one or more of the volumetric flow rate over time, a fluidic resistance of the patient line region detected by a steady-state measurement, a fluidic resistance of the catheter region detected by a steady-state measurement, a fluidic resistance of the patient line region detected by a measurement of a transient component of the measured pressures over time, a fluidic resistance of the catheter region detected by a measurement of the transient component of the measured pressures over time, and a characteristic frequency of the transient component of the measured pressures over time.

In some implementations, the fluid capacitive element includes an elastomeric material that is distended by pressure in the medical tube.

In some implementations, the fluid capacitive element is an elastomeric segment of the medical tube.

In some implementations, the fluid capacitive element has a distensibility that is substantially greater than a distensibility of the medical tube.

In some implementations, the fluid capacitive element is configured to store additional fluid volume relative to the medical tube with a concomitant increase in pressure.

In another aspect, a method includes providing or withdrawing a volume of fluid to or from a first portion of a distensible medical tube connected to a medical device. An occlusion is present in the medical tube at a location that defines a boundary between the first portion and a second portion of the medical tube. The method also includes measuring two pressures of the fluid in the first portion of the medical tube while the volume of fluid is being provided or withdrawn. The method also includes determining a length of the first portion of the medical tube based on a difference between the two pressure measurements and an amount of time elapsed between the two pressure measurements.

Implementations can include one or more of the following features.

In some implementations, the medical device includes a dialysis machine.

In some implementations, the dialysis machine includes a PD machine.

In some implementations, the length of the first portion represents the location of the occlusion relative to a proximal end of the medical tube connected to the medical device.

In some implementations, the two pressures are measured by a pressure sensor at a proximal end of the medical tube connected to the medical device.

In some implementations, the fluid is at least partially blocked by the occlusion.

In some implementations, the fluid being at least partially blocked by the occlusion causes an increase or a decrease in pressure in the medical tube.

In some implementations, the fluid being at least partially blocked by the occlusion causes a distension in the medical tube.

In some implementations, the medical tube includes a catheter at a distal end of the medical tube.

In some implementations, the method includes inferring a type of the occlusion based at least in part on a determined location of the occlusion.

In some implementations, the type of the occlusion includes one or more of a pinch of the medical tube, a kink in the medical tube, a deposit in the medical tube, and a deposit blocking a hole of a catheter in the catheter region at a distal end of the medical tube.

In some implementations, the method includes determining the length of the first portion of the medical tube based on one or more of dimensions of the medical tube, a material composition of the medical tube, and the volume of fluid provided to or withdrawn from the first portion of the medical tube.

In some implementations, the determination of the length of the first portion of the medical tube is based on a fluidic capacitance of the medical tube.

In some implementations, the difference between the two pressure measurements and the amount of time elapsed between the two pressure measurements includes a slope of a portion of a pressure waveform, the portion of the pressure waveform corresponding to times during which the volume of fluid is being provided or withdrawn.

In another aspect, a method includes providing or withdrawing a volume of fluid to or from a first portion of a distensible medical tube connected to a medical device. An occlusion is present in the medical tube at a location that defines a boundary between the first portion and a second portion of the medical tube. The method also includes measuring a first pressure of the fluid in the first portion of the medical tube before the providing or withdrawing of the volume of fluid is abruptly stopped. The method also includes measuring a plurality of pressures over time of the fluid in the first portion of the medical tube after the providing or withdrawing of the volume of fluid is abruptly stopped. The method also includes determining a length of the first portion of the medical tube based on an elapsed time between the first pressure measurement and a second pressure measurement of the plurality of pressure measurements over time.

Implementations can include one or more of the following features.

In some implementations, the medical device includes a dialysis machine.

In some implementations, the dialysis machine includes a PD machine.

In some implementations, the first pressure measurement represents an initial steady-state pressure.

In some implementations, the method includes identifying a final steady-state pressure of the plurality of pressure measurements.

In some implementations, the second pressure measurement is approximately 36.8% of a difference between the first pressure measurement and the final steady-state pressure measurement.

In some implementations, the second pressure measurement is approximately 36.8% of a difference between the first pressure measurement and the final steady-state pressure measurement plus the final steady-state pressure measurement.

In some implementations, the length of the first portion represents the location of the occlusion relative to a proximal end of the medical tube connected to the medical device.

In some implementations, the first pressure and the second pressure are measured by a pressure sensor at a proximal end of the medical tube connected to the medical device.

In some implementations, the fluid is at least partially blocked by the occlusion.

In some implementations, the fluid being at least partially blocked by the occlusion causes an increase or a decrease in pressure in the medical tube.

In some implementations, the fluid being at least partially blocked by the occlusion causes a distension in the medical tube.

In some implementations, the medical tube includes a catheter at a distal end of the medical tube.

In some implementations, the method includes inferring a type of the occlusion based at least in part on a determined location of the occlusion.

In some implementations, the type of the occlusion includes one or more of a pinch of the medical tube, a kink in the medical tube, a deposit in the medical tube, and a deposit blocking a hole of a catheter at a distal end of the medical tube.

In some implementations, the deposit includes omental fat.

In some implementations, the method includes determining the length of the first portion of the medical tube based on one or more of dimensions of the medical tube, a material composition of the medical tube, and a volumetric flow rate of the volume of fluid provided to or withdrawn from the first portion of the medical tube.

In some implementations, the determination of the length of the first portion of the medical tube is based on a fluidic capacitance of the medical tube.

In another aspect, a medical device includes a distensible medical tube having a proximal end connected to a port of the medical device. An occlusion is present in the medical tube at a location that defines a boundary between a first portion of the medical tube and a second portion of the medical tube. The medical device also includes a pressure sensor at the proximal end of the medical tube. The pressure sensor is configured for measuring a first pressure of fluid in the first portion of the medical tube.

The medical device also includes one or more pumps configured for providing or withdrawing a volume of fluid to or from the first portion of the medical tube. The pressure sensor is configured for measuring a second pressure of the fluid in the first portion of the medical tube. The medical device also includes a processor configured for determining a length of the first portion of the medical tube based on a difference between the second pressure and the first pressure.

Implementations can include one or more of the following features.

In some implementations, the medical device includes a dialysis machine.

In some implementations, the dialysis machine includes a PD machine.

In some implementations, the length of the first portion represents the location of the occlusion relative to the proximal end of the medical tube.

In some implementations, the medical tube includes a catheter at a distal end of the medical tube.

In some implementations, the processor is configured to infer a type of the occlusion based at least in part on a determined location of the occlusion.

In some implementations, the processor is configured to determine the length of the first portion of the medical tube based on one or more of dimensions of the medical tube, a material composition of the medical tube, a fluid capacitance of the medical tube, and the volume of fluid provided to or withdrawn from the first portion of the medical tube.

In another aspect, a medical device includes a distensible medical tube connected to a port of the medical device. The medical tube includes a patient line region and a catheter region separated by a fluid capacitive element. The medical device also includes one or more pumps configured for providing or withdrawing a fluid to or from the medical tube at a volumetric flow rate over time. The medical device also includes a pressure sensor at the patient line region. The pressure sensor is configured for measuring a plurality of pressures over time of the fluid. The medical device also includes a processor configured for determining whether an occlusion in the medical tube is present in the patient line region or the catheter region based on the measured pressures over time.

Implementations can include one or more of the following features.

In some implementations, the medical device includes a dialysis machine.

In some implementations, the dialysis machine includes a PD machine.

In some implementations, the volumetric flow rate over time includes a dispensing or withdrawing step of fluid that is abruptly stopped.

In some implementations, the medical tube includes a catheter in the catheter region at a distal end of the medical tube.

In some implementations, the processor is configured to infer a type of the occlusion based at least in part on a determined location of the occlusion.

In some implementations, the processor is configured to determine whether the occlusion in the medical tube is present in the patient line region or the catheter region based on one or more of the volumetric flow rate over time, a fluidic resistance of the patient line region detected by a steady-state measurement, a fluidic resistance of the catheter region detected by a steady-state measurement, a fluidic resistance of the patient line region detected by a measurement of a transient component of the measured pressures over time, a fluidic resistance of the catheter region detected by a measurement of the transient component of the measured pressures over time, and a characteristic frequency of the transient component of the measured pressures over time.

In some implementations, the fluid capacitive element includes an elastomeric material that is distended by pressure in the medical tube.

In some implementations, the fluid capacitive element is an elastomeric segment of the medical tube.

In some implementations, the fluid capacitive element has a distensibility that is substantially greater than a distensibility of the medical tube.

In some implementations, the fluid capacitive element is configured to store additional fluid volume relative to the medical tube with a concomitant increase in pressure.

In another aspect, a medical device includes a distensible medical tube having a proximal end connected to a port of the medical device. An occlusion is present in the medical tube at a location that defines a boundary between a first portion of the medical tube and a second portion of the medical tube. The medical device also includes one or more pumps configured for providing or withdrawing a volume of fluid to or from the first portion of the medical tube. The medical device also includes a pressure sensor at the proximal end of the medical tube. The pressure sensor is configured for measuring two pressures of the fluid in the first portion of the medical tube while the volume of fluid is being provided or withdrawn. The medical device also includes a processor configured for determining a length of the first portion of the medical tube based on a difference between the two pressure measurements and an amount of time elapsed between the two pressure measurements.

Implementations can include one or more of the following features.

In some implementations, the medical device includes a dialysis machine.

In some implementations, the dialysis machine includes a PD machine.

In some implementations, the length of the first portion represents the location of the occlusion relative to the proximal end of the medical tube.

In some implementations, the medical tube includes a catheter at a distal end of the medical tube.

In some implementations, the processor is configured to infer a type of the occlusion based at least in part on a determined location of the occlusion.

In some implementations, the processor is configured to determine the length of the first portion of the medical tube based on one or more of dimensions of the medical tube, a material composition of the medical tube, a fluid capacitance of the medical tube, and the volume of fluid provided to or withdrawn from the first portion of the medical tube.

In some implementations, the difference between the two pressure measurements and the amount of time elapsed between the two pressure measurements includes a slope of a portion of a pressure waveform. The portion of the pressure waveform corresponds to times during which the volume of fluid is being provided or withdrawn.

In another aspect, a medical device includes a distensible medical tube having a proximal end connected to a port of the medical device. An occlusion is present in the medical tube at a location that defines a boundary between a first portion of the medical tube and a second portion of the medical tube. The medical device also includes one or more pumps configured for providing or withdrawing a volume of fluid to or from the first portion of the medical tube. The medical device also includes a pressure sensor at the proximal end of the medical tube. The pressure sensor configured for measuring a first pressure of the fluid in the first portion of the medical tube before the providing or withdrawing of the volume of fluid is abruptly stopped, and measuring a plurality of pressures over time of the fluid in the first portion of the medical tube after the providing or withdrawing of the volume of fluid is abruptly stopped. The medical device also includes a processor configured for determining a length of the first portion of the medical tube based on an elapsed time between the first pressure measurement and a second pressure measurement of the plurality of pressure measurements over time.

Implementations can include one or more of the following features.

In some implementations, the medical device includes a dialysis machine.

In some implementations, the dialysis machine includes a PD machine.

In some implementations, the processor is configured to identify a final steady-state pressure of the plurality of pressure measurements.

In some implementations, the second pressure measurement is approximately 36.8% of a difference between the first pressure measurement and the final steady-state pressure measurement plus the final steady-state pressure measurement.

In some implementations, the length of the first portion represents the location of the occlusion relative to the proximal end of the medical tube.

In some implementations, the medical tube includes a catheter at a distal end of the medical tube.

In some implementations, the processor is configured to infer a type of the occlusion based at least in part on a determined location of the occlusion.

In some implementations, the processor is configured to determine the length of the first portion of the medical tube based on one or more of dimensions of the medical tube, a material composition of the medical tube, a fluidic capacitance of the medical tube, and a volumetric flow rate of the volume of fluid provided to or withdrawn from the first portion of the medical tube.

Implementations can include one or more of the following advantages.

In some implementations, the systems and techniques described herein can be used to determine a location of an occlusion in the medical tube (e.g., in a patient line or in the catheter). The type of occlusion can be inferred based on the determined location. The dialysis machine can determine an appropriate response for addressing the particular type of occlusion, including emitting an alert indicating the presence of the occlusion and/or adjusting one or more operating parameters of the dialysis machine in an attempt to clear the occlusion and/or to modulate the flow in the medical tube to avoid an overpressure condition.

In some implementations, the dialysis machine is configured to determine the location of the occlusion using the pressure sensor built into the dialysis machine without requiring a separate pressure sensor.

Other aspects, features, and advantages of the invention will be apparent from the description and drawings, and from the claims.

DESCRIPTION OF DRAWINGS

Like reference symbols in the various drawings indicate like elements.

DETAILED DESCRIPTION

A dialysis machine (e.g., a peritoneal dialysis (PD) machine) can include a pressure sensor mounted at a proximal end of a patient line made of a distensible material (e.g., an elastomeric patient line) that provides PD solution to a patient through a catheter. During treatment, an occlusion can occur at different locations in the patient line and/or the catheter. When an incremental volume $\Delta V_f$ of additional solution is provided to the patient line while the occlusion is present, a change in pressure $\Delta P$ (e.g., a pressure rise) results. The change in pressure $\Delta P$ depends on the dimensions and the distensibility of the non-occluded portion of the patient line. If the change in pressure $\Delta P$, the incremental volume $\Delta V_f$, the properties related to the distensibility of the patient line, and some of the dimensions of the patient line are known, the location of the occlusion (e.g., the distance x between the patient line port and the occlusion) can be inferred. Because some types of occlusions typically occur in certain parts of the patient line, the occlusion type can be inferred based on the determined location.

In some implementations, the location of the occlusion can be determined by measuring a change in pressure measurements over time while an additional volume of solution is provided to the patient line. In some implementations, the location of the occlusion can be determined by measuring an amount of time required for pressure measurements to decay below a predetermined threshold after an additional volume of solution is provided to the patient line.

In some implementations, the patient line may include a fluid capacitive element that is located between a patient line region and a catheter region of the patient line. The fluidic capacitive element may have a distensibility that is substantially greater than that of the patient line itself. Accordingly, occlusions that occur between the dialysis machine and the fluid capacitive element do not cause the pressure sensor to experience the effects of the fluid capacitive element, and occlusions that occur between the fluid capacitive element and the tip of the catheter do cause the pressure sensor to experience the effects of the fluid capacitive element. That is, the fluid capacitive element may be positioned strategically such that the generated information can localize the occlusion to a region of particular interest. For example, by analyzing characteristics of a plurality of pressure measurements over time, including steady-state measurements and measurements of a transient (e.g., fluctuating) component of the measured pressures over time, a determination can be made as to whether the occlusion is present in the patient line region (e.g., outside of the patient) or the catheter region (e.g., inside the patient).

Figure 1:
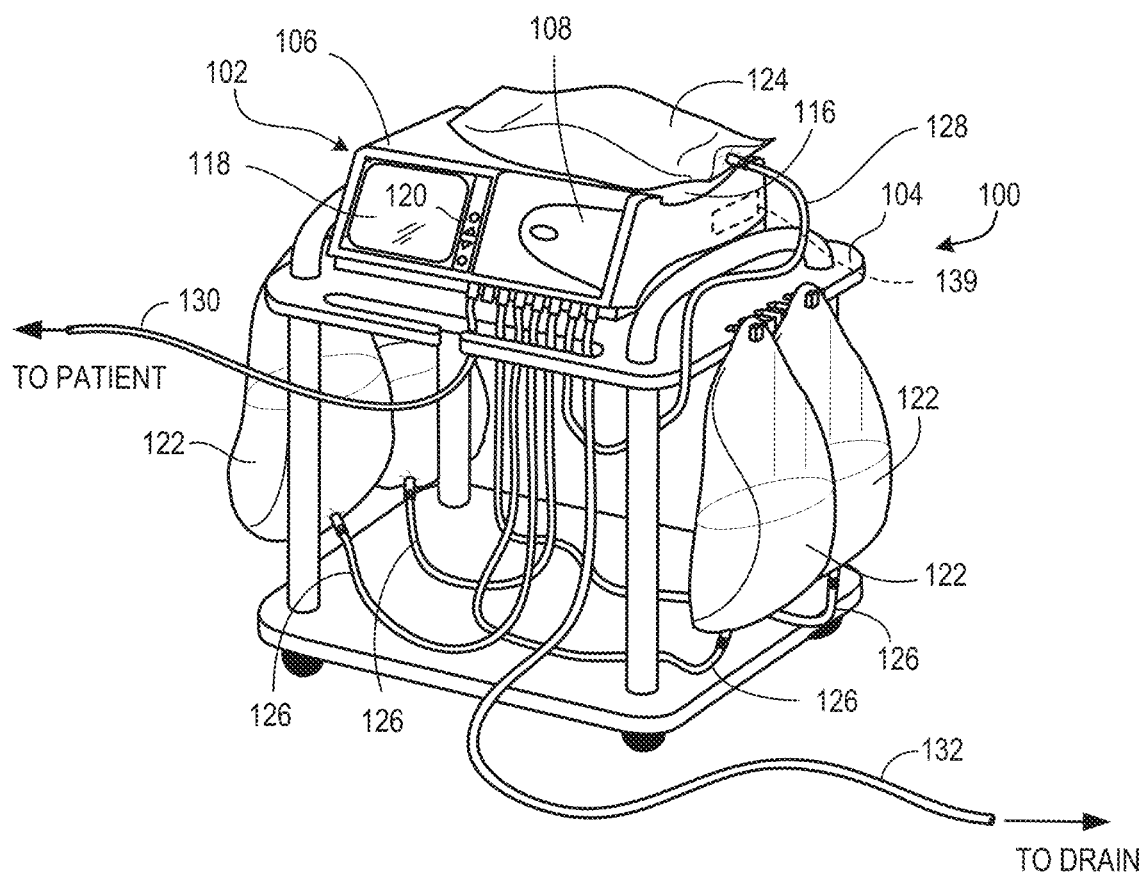
FIG. 1 shows an example of a peritoneal dialysis (PD) system.
Figure 2:
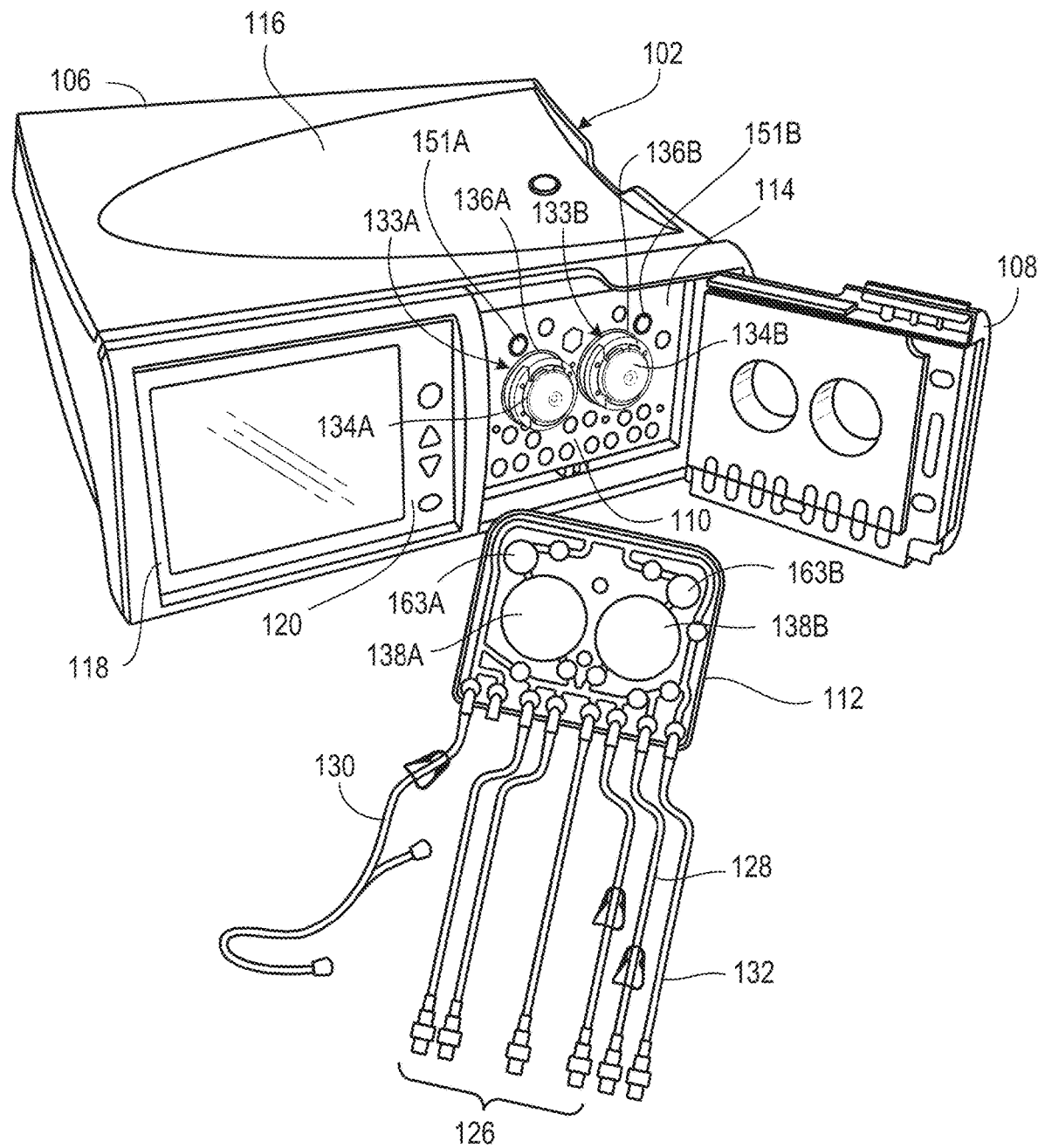
FIG. 2 is a perspective view of a PD cycler and a PD cassette of the PD system of FIG. 1, with a door of the PD cycler in the open position to show the inner surfaces of the PD cycler that interface with the PD cassette during use.

FIG. 1 shows a PD system 100 that includes a PD machine (also generally referred to as a PD cycler) 102 seated on a cart 104. Referring also to FIG. 2, the PD machine 102 includes a housing 106, a door 108, and a cassette interface 110 that contacts a disposable PD cassette 112 when the cassette 112 is disposed within a cassette compartment 114 formed between the cassette interface 110 and the closed door 108. A heater tray 116 is positioned on top of the housing 106. The heater tray 116 is sized and shaped to accommodate a bag of PD solution such as dialysate (e.g., a 5 liter bag of dialysate). The PD machine 102 also includes a user interface such as a touch screen display 118 and additional control buttons 120 that can be operated by a user (e.g., a caregiver or a patient) to allow, for example, set up, initiation, and/or termination of a PD treatment.

Dialysate bags 122 are suspended from fingers on the sides of the cart 104, and a heater bag 124 is positioned in the heater tray 116. The dialysate bags 122 and the heater bag 124 are connected to the cassette 112 via dialysate bag lines 126 and a heater bag line 128, respectively. The dialysate bag lines 126 can be used to pass dialysate from dialysate bags 122 to the cassette 112 during use, and the heater bag line 128 can be used to pass dialysate back and forth between the cassette 112 and the heater bag 124 during use. In addition, a patient line 130 and a drain line 132 are connected to the cassette 112. The patient line 130 can be connected to a patient's abdomen via a catheter (e.g., the catheter 1002 of FIG. 10) and can be used to pass dialysate back and forth between the cassette 112 and the patient's peritoneal cavity during use. The catheter 1002 may be connected to the patient line 130 via a port (1004 of FIG. 10) such as a fitting. The drain line 132 can be connected to a drain or drain receptacle and can be used to pass dialysate from the cassette 112 to the drain or drain receptacle during use.

The PD machine 102 also includes a control unit 139 (e.g., a processor). The control unit 139 can receive signals from and transmit signals to the touch screen display 118, the control panel 120, and the various other components of the PD system 100. The control unit 139 can control the operating parameters of the PD machine 102. In some implementations, the control unit 139 is an MPC823 PowerPC device manufactured by Motorola, Inc.

Figure 3:
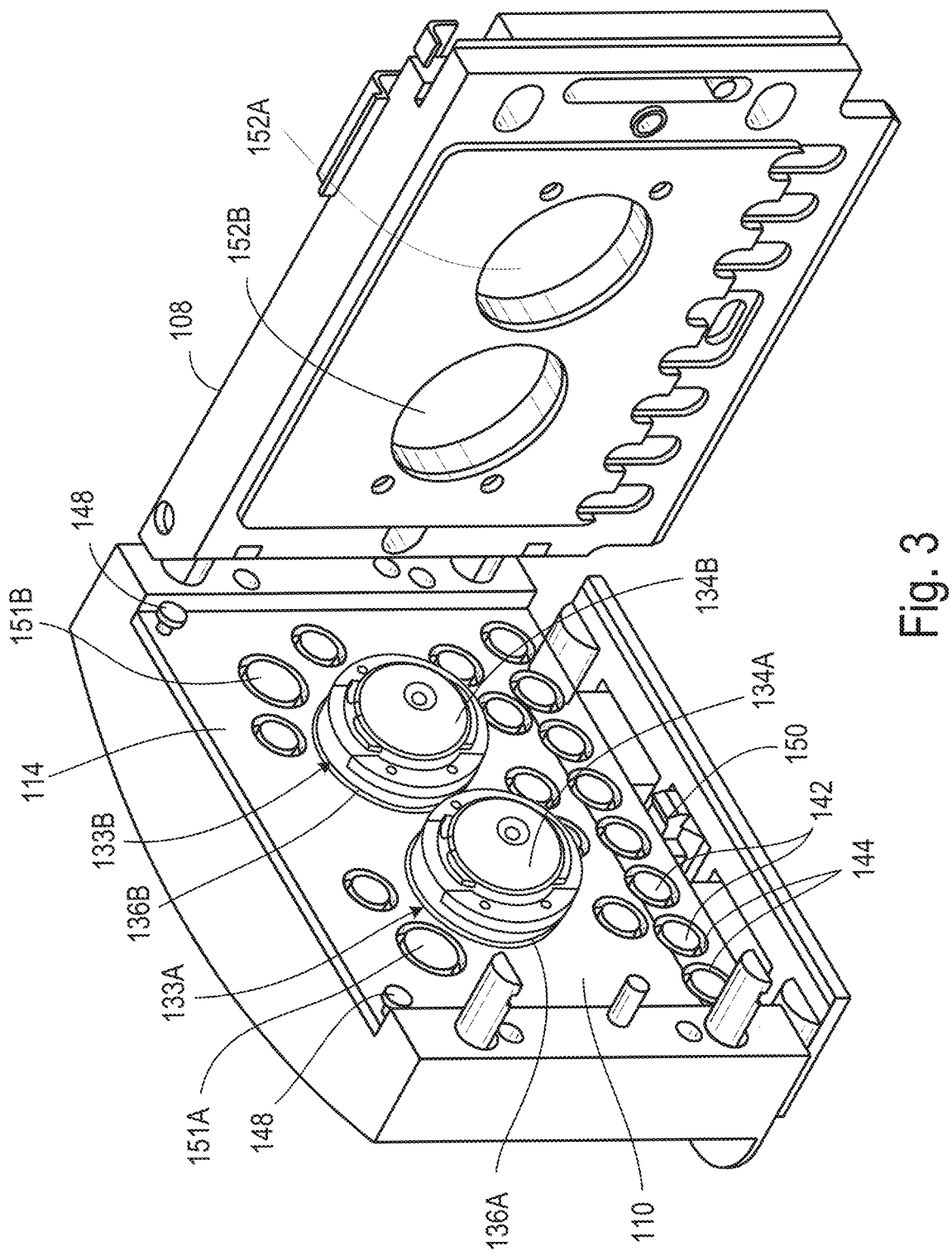
FIG. 3 is a perspective view of an open cassette compartment of the PD cycler of FIG. 1.

FIG. 3 shows a more detailed view of the cassette interface 110 and the door 108 of the PD machine 102. As shown, the PD machine 102 includes pistons 133A, 133B with piston heads 134A, 134B attached to piston shafts 135A, 135B (piston shaft 135A shown in FIGS. 9A-G) that can be axially moved within piston access ports 136A, 136B formed in the cassette interface 110. The pistons 133A, 133B, piston heads 134A, 134B, and piston shafts 135A, 135B are sometimes referred to herein as pumps. The piston shafts 135A, 135B are connected to stepper motors that can be operated to move the pistons 133A, 133B axially inward and outward such that the piston heads 134A, 134B move axially inward and outward within the piston access ports 136A, 136B. The stepper motors drive lead screws, which move nuts inward and outward along the lead screws. The stepper motors may be controlled by driver modules (e.g., the driver modules 1538a, 1538b of FIG. 15). The nuts, in turn, are connected to the pistons 133A, 133B and thus cause the pistons 133A, 133B to move inward and outward as the stepper motors rotate the lead screws. Stepper motor controllers (e.g., the microcontroller 1436 of FIG. 14) provide the necessary current to be driven through the windings of the stepper motors to move the pistons 133A, 133B. The polarity of the current determines whether the pistons 133A, 133B are advanced or retracted. In some implementations, the stepper motors require 200 steps to make a full rotation, and this corresponds to 0.048 inch of linear travel.

The PD system 100 also includes encoders (e.g., optical encoders) that measure the rotational movement of the lead screws. The axial positions of the pistons 133A, 133B can be determined based on the rotational movement of the lead screws, as determined by the encoders. Thus, the measurements of the encoders can be used to accurately position the piston heads 134A, 134B of the pistons 133A, 133B.

As discussed below, when the cassette 112 (shown in FIGS. 2 and 4-7) is positioned within the cassette compartment 114 of the PD machine 102 with the door 108 closed, the piston heads 134A, 134B of the PD machine 102 align with pump chambers 138A, 138B of the cassette 112 such that the piston heads 134A, 134B can be mechanically connected to dome-shaped fastening members 161A, 161B of the cassette 112 overlying the pump chambers 138A, 138B. As a result of this arrangement, movement of the piston heads 134A, 134B toward the cassette 112 during treatment can decrease the volume of the pump chambers 138A, 138B and force dialysate out of the pump chambers 138A, 138B, while retraction of the piston heads 134A, 134B away from the cassette 112 can increase the volume of the pump chambers 138A, 138B and cause dialysate to be drawn into the pump chambers 138A, 138B.

As shown in FIG. 3, the cassette interface 110 includes two pressure sensors 151A, 151B that align with pressure sensing chambers 163A, 163B (shown in FIGS. 2, 4, 6, and 7) of the cassette 112 when the cassette 112 is positioned within the cassette compartment 114. Portions of a membrane 140 of the cassette 112 that overlie the pressure sensing chambers 163A, 163B adhere to the pressure sensors 151A, 151B using vacuum pressure. Specifically, clearance around the pressure sensors 151A, 151B communicates vacuum to the portions of the cassette membrane 140 overlying the pressure sensing chambers 163A, 163B to hold those portions of the cassette membrane 140 tightly against the pressure sensors 151A, 151B. The pressure of fluid within the pressure sensing chambers 163A, 163B causes the portions of the cassette membrane 140 overlying the pressure sensing chambers 163A, 163B to contact and apply pressure to the pressure sensors 151A, 151B.

The pressure sensors 151A, 151B can be any sensors that are capable of measuring the fluid pressure in the sensing chambers 163A, 163B. In some implementations, the pressure sensors are solid state silicon diaphragm infusion pump force/pressure transducers. One example of such a sensor is the Model 1865 force/pressure transducer manufactured by Sensym Foxboro ICT. In some implementations, the force/pressure transducer is modified to provide increased voltage output. The force/pressure transducer can, for example, be modified to produce an output signal of 0 to 5 volts.

Still referring to FIG. 3, the PD machine 102 also includes multiple inflatable members 142 positioned within inflatable member ports 144 in the cassette interface 110. The inflatable members 142 align with depressible dome regions 146 of the cassette 112 (shown in FIGS. 4-6) when the cassette 112 is positioned within the cassette compartment 114 of the PD machine 102. While only a couple of the inflatable members 142 are labeled in FIG. 3, it should be understood that the PD machine 102 includes an inflatable member 142 associated with each of the depressible dome regions 146 of the cassette 112. The inflatable members 142 act as valves to direct dialysate through the cassette 112 in a desired manner during use. In particular, the inflatable members 142 bulge outward beyond the surface of the cassette interface 110 and into contact with the depressible dome regions 146 of the cassette 112 when inflated, and retract into the inflatable member ports 144 and out of contact with the cassette 112 when deflated. By inflating certain inflatable members 142 to depress their associated dome regions 146 on the cassette 112, certain fluid flow paths within the cassette 112 can be occluded. Thus, dialysate can be pumped through the cassette 112 by actuating the piston heads 134A, 134B, and can be guided along desired flow paths within the cassette 112 by selectively inflating and deflating the various inflatable members 142.

Still referring to FIG. 3, locating pins 148 extend from the cassette interface 110 of the PD machine 102. When the door 108 is in the open position, the cassette 112 can be loaded onto the cassette interface 110 by positioning the top portion of the cassette 112 under the locating pins 148 and pushing the bottom portion of the cassette 112 toward the cassette interface 110. The cassette 112 is dimensioned to remain securely positioned between the locating pins 148 and a spring loaded latch 150 extending from the cassette interface 110 to allow the door 108 to be closed over the cassette 112.

The locating pins 148 help to ensure that proper alignment of the cassette 112 within the cassette compartment 114 is maintained during use.

The door 108 of the PD machine 102, as shown in FIG. 3, defines cylindrical recesses 152A, 152B that substantially align with the pistons 133A, 133B when the door 108 is in the closed position. When the cassette 112 (shown in FIGS. 4-7) is positioned within the cassette compartment 114, hollow projections 154A, 154B of the cassette 112, inner surfaces of which partially define the pump chambers 138A, 138B, fit within the recesses 152A, 152B. The door 108 further includes a pad that is inflated during use to compress the cassette 112 between the door 108 and the cassette interface 110. With the pad inflated, the portions of the door 108 forming the recesses 152A, 152B support the projections 154A, 154B of the cassette 112 and the planar surface of the door 108 supports the other regions of the cassette 112. The door 108 can counteract the forces applied by the inflatable members 142 and thus allows the inflatable members 142 to actuate the depressible dome regions 146 on the cassette 112. The engagement between the door 108 and the hollow projections 154A, 154B of the cassette 112 can also help to hold the cassette 112 in a desired fixed position within the cassette compartment 114 to further ensure that the pistons 133A, 133B align with the fluid pump chambers 138A, 138B of the cassette 112.

The control unit (139 of FIG. 1) is connected to the pressure sensors 151A, 151B, to the stepper motors (e.g., the drivers of the stepper motors) that drive the pistons 133A, 133B, and to the encoders that monitor rotation of the lead screws of the stepper motors such that the control unit 139 can receive signals from and transmit signals to those components of the system. The control unit 139 monitors the components to which it is connected to determine whether any complications exists within the PD system 100, such as the presence of an occlusion.

Figure 4:
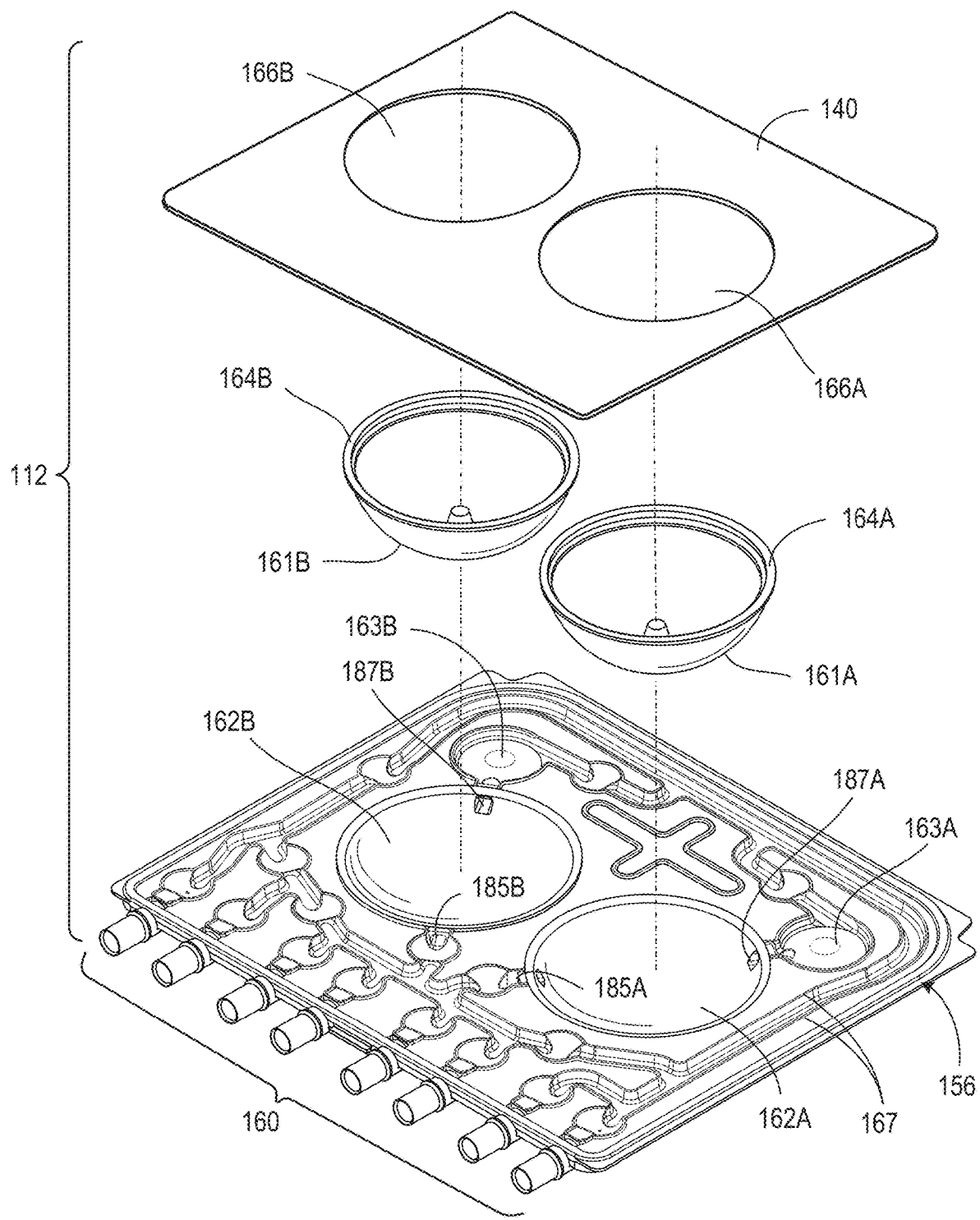
FIG. 4 is an exploded, perspective view of the PD cassette of FIG. 2, which includes dome-shaped fastening members that can be mechanically connected to piston heads of the PD cycler of FIG. 1.
Figure 5:
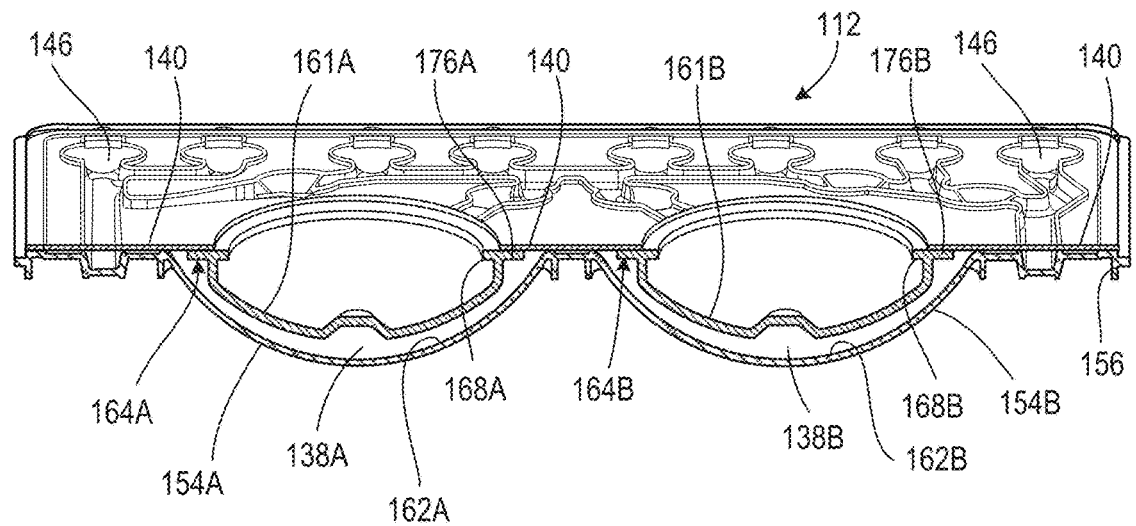
FIG. 5 is a cross-sectional view of the fully assembled PD cassette of FIG. 4.
Figure 6:
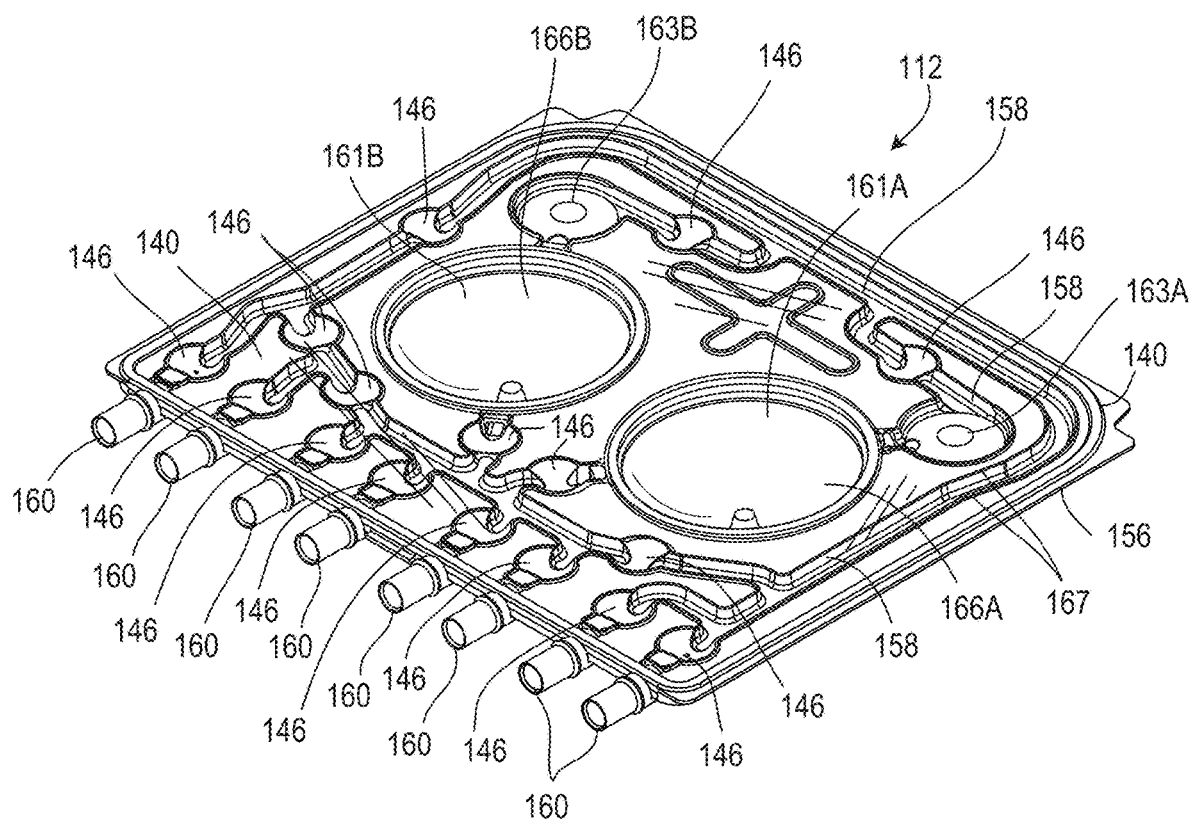
FIG. 6 is a perspective view of the fully assembled PD cassette of FIG. 4, from a flexible membrane and dome-shaped fastening member side of the PD cassette.
Figure 7:
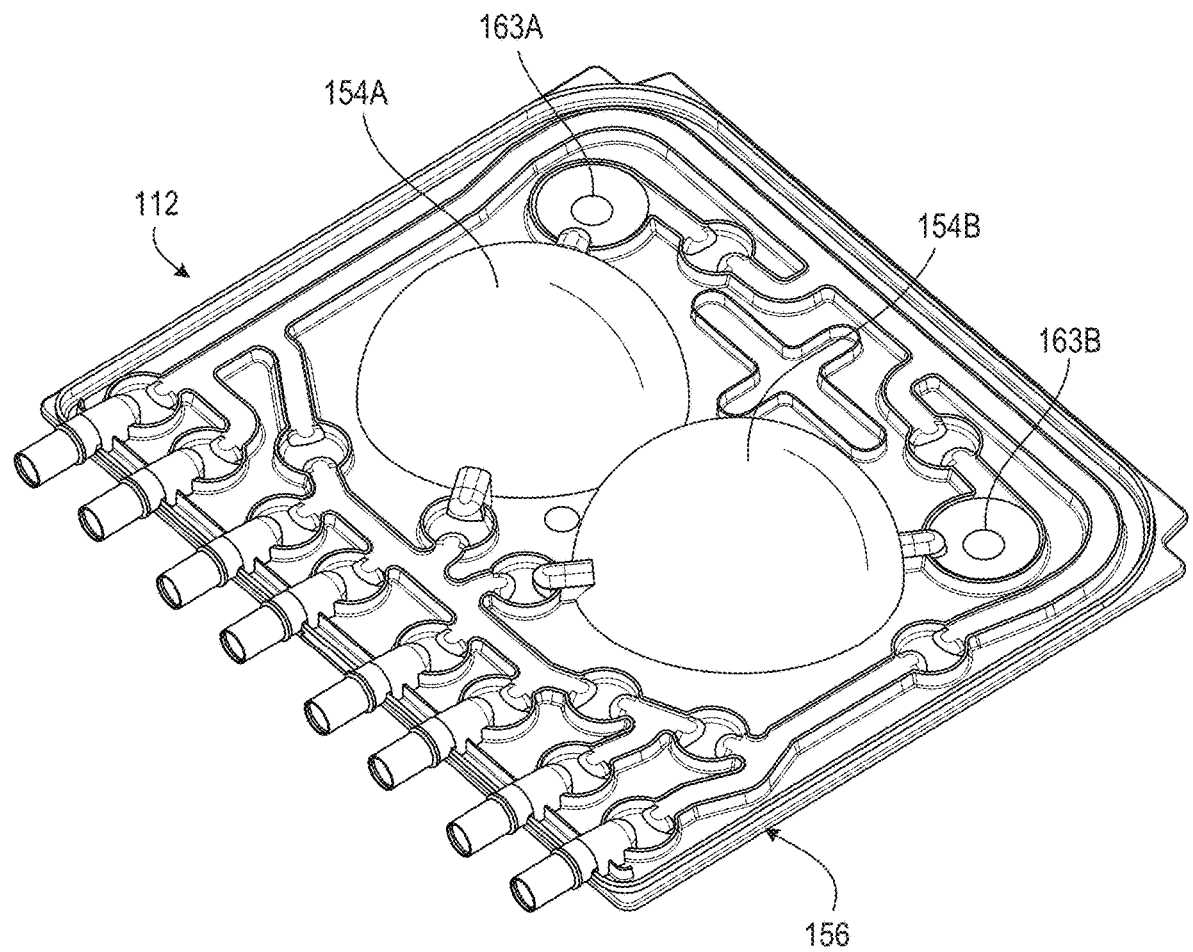
FIG. 7 is a perspective view of the fully assembled PD cassette of FIG. 4, from a rigid base side of the PD cassette.

FIG. 4 is an exploded, perspective view of the cassette 112, FIG. 5 is a cross-sectional view of the fully assembled cassette 112, and FIGS. 6 and 7 are perspective views of the assembled cassette 112, from the membrane side and from the rigid base side, respectively. Referring to FIGS. 4-6, the flexible membrane 140 of the cassette 112 is attached to a periphery of the tray-like rigid base 156. Rigid dome-shaped fastening members 161A, 161B are positioned within recessed regions 162A, 162B of the base 156. The dome-shaped fastening members 161A, 161B are sized and shaped to receive the piston heads 134A, 134B of the PD machine 102. In some implementations, the dome-shaped fastening members 161A, 161B have a diameter, measured from the outer edges of flanges 164A, 164B, of about 1.5 inches to about 2.5 inches (e.g., about 2.0 inches) and take up about two-thirds to about three-fourths of the area of the recessed regions 162A, 162B. The annular flanges 164A, 164B of the rigid dome-shaped fastening members 161A, 161B are attached in a liquid-tight manner to portions of the inner surface of the membrane 140 surrounding substantially circular apertures 166A, 166B formed in the membrane 140. The annular flanges 164A, 164B of the rigid dome-shaped fastening members 161A, 161B can, for example, be thermally bonded or adhesively bonded to the membrane 140. The apertures 166A, 166B of the membrane 140 expose the rigid dome-shaped fastening members 161A, 161B such that the piston heads 134A, 134B are able to directly contact and mechanically connect to the dome-shaped fastening members 161A, 161B during use.

The annular flanges 164A, 164B of the dome-shaped fastening members 161A, 161B, as shown in FIG. 5, form annular projections 168A, 168B that extend radially inward and annular projections 176A, 176B that extend radially outward from the side walls of the dome-shaped fastening members 161A, 161B. When the piston heads 134A, 134B are mechanically connected to the dome-shaped fastening members 161A, 161B, the radially inward projections 168A, 168B engage the rear angled surfaces of the sliding latches 145A, 147A of the piston heads 134A, 134B to firmly secure the dome-shaped fastening members 161A, 161B to the piston heads 134A, 134B. Because the membrane 140 is attached to the dome-shaped fastening members 161A, 161B, movement of the dome-shaped fastening members 161A, 161B into and out of the recessed regions 162A, 162B of the base 156 (e.g., due to reciprocating motion of the pistons 133A, 133B) causes the flexible membrane 140 to similarly be moved into and out of the recessed regions 162A, 162B of the base 156. This movement allows fluid to be forced out of and drawn into the fluid pump chambers 138A, 138B, which are formed between the recessed regions 162A, 162B of the base 156 and the portions of the dome-shaped fastening members 161A, 161B and membrane 140 that overlie those recessed regions 162A, 162B.

Referring to FIGS. 4 and 6, raised ridges 167 extend from the substantially planar surface of the base 156 towards and into contact with the inner surface of the flexible membrane 140 when the cassette 112 is compressed between the door 108 and the cassette interface 110 of the PD machine 102 to form a series of fluid passageways 158 and to form the multiple, depressible dome regions 146, which are widened portions (e.g., substantially circular widened portions) of the fluid pathways 158, as shown in FIG. 6. The fluid passageways 158 fluidly connect the fluid line connectors 160 of the cassette 112, which act as inlet/outlet ports of the cassette 112, to the fluid pump chambers 138A, 138B. As noted above, the various inflatable valve members 142 of the PD machine 102 act on the cassette 112 during use. During use, the dialysate flows to and from the pump chambers 138A, 138B through the fluid pathways 158 and dome regions 146. At each depressible dome region 146, the membrane 140 can be deflected to contact the planar surface of the base 156 from which the raised ridges 167 extend. Such contact can substantially impede (e.g., prevent) the flow of dialysate along the region of the pathway 158 associated with that dome region 146. Thus, the flow of dialysate through the cassette 112 can be controlled through the selective depression of the depressible dome regions 146 by selectively inflating the inflatable members 142 of the PD machine 102.

Still referring to FIGS. 4 and 6, the fluid line connectors 160 are positioned along the bottom edge of the cassette 112. As noted above, the fluid pathways 158 in the cassette 112 lead from the pumping chambers 138A, 138B to the various connectors 160. The connectors 160 are positioned asymmetrically along the width of the cassette 112. The asymmetrical positioning of the connectors 160 helps to ensure that the cassette 112 will be properly positioned in the cassette compartment 114 with the membrane 140 of the cassette 112 facing the cassette interface 110. The connectors 160 are configured to receive fittings on the ends of the dialysate bag lines 126, the heater bag line 128, the patient line 130, and the drain line 132. One end of the fitting can be inserted into and bonded to its respective line and the other end can be inserted into and bonded to its associated connector 160. By permitting the dialysate bag lines 126, the heater bag line 128, the patient line 130, and the drain line 132 to be connected to the cassette, as shown in FIGS. 1 and 2, the connectors 160 allow dialysate to flow into and out of the cassette 112 during use. As the pistons 133A, 133B are reciprocated, the inflatable members 142 can be selectively inflated to allow fluid to flow from any of the lines 126, 128, 130, and 132 to any of ports 185A, 185B, 187A, and 187B of the pump chambers 138A, 138B, and vice versa.

The rigidity of the base 156 helps to hold the cassette 112 in place within the cassette compartment 114 of the PD machine 102 and to prevent the base 156 from flexing and deforming in response to forces applied to the projections 154A, 154B by the dome-shaped fastening members 161A, 161B and in response to forces applied to the planar surface of the base 156 by the inflatable members 142. The dome-shaped fastening members 161A, 161B are also sufficiently rigid that they do not deform as a result of usual pressures that occur in the pump chambers 138A, 138B during the fluid pumping process. Thus, the deformation or bulging of the annular portions 149A, 149B of the membrane 140 can be assumed to be the only factor other than the movement of the pistons 133A, 133B that affects the volume of the pump chambers 138A, 138B during the pumping process.

The base 156 and the dome-shaped fastening members 161A, 161B of the cassette 112 can be formed of any of various relatively rigid materials. In some implementations, these components of the cassette 112 are formed of one or more polymers, such as polypropylene, polyvinyl chloride, polycarbonate, polysulfone, and other medical grade plastic materials. In some implementations, these components can be formed of one or more metals or alloys, such as stainless steel. These components of can alternatively be formed of various different combinations of the above-noted polymers and metals. These components of the cassette 112 can be formed using any of various different techniques, including machining, molding, and casting techniques.

As noted above, the membrane 140 is attached to the periphery of the base 156 and to the annular flanges 164A, 164B of the dome-shaped fastening members 161A, 161B. The portions of the membrane 140 overlying the remaining portions of the base 156 are typically not attached to the base 156. Rather, these portions of the membrane 140 sit loosely atop the raised ridges 165A, 165B, and 167 extending from the planar surface of the base 156. Any of various attachment techniques, such as adhesive bonding and thermal bonding, can be used to attach the membrane 140 to the periphery of the base 156 and to the dome-shaped fastening members 161A, 161B. The thickness and material(s) of the membrane 140 are selected so that the membrane 140 has sufficient flexibility to flex toward the base 156 in response to the force applied to the membrane 140 by the inflatable members 142. In some implementations, the membrane 140 is about 0.100 micron to about 0.150 micron in thickness. However, various other thicknesses may be sufficient depending on the type of material used to form the membrane 140.

Any of various different materials that permit the membrane 140 to deflect in response to movement of the inflatable members 142 without tearing can be used to form the membrane 140. In some implementations, the membrane 140 includes a three-layer laminate. In some implementations, for example, inner and outer layers of the laminate are formed of a compound that is made up of 60 percent Septon® 8004 thermoplastic rubber (i.e., hydrogenated styrenic block copolymer) and 40 percent ethylene, and a middle layer is formed of a compound that is made up of 25 percent Tuftec® H1062 (SEBS: hydrogenated styrenic thermoplastic elastomer), 40 percent Engage® 8003 polyolefin elastomer (ethylene octene copolymer), and 35 percent Septon® 8004 thermoplastic rubber (i.e., hydrogenated styrenic block copolymer). The membrane can alternatively include more or fewer layers and/or can be formed of different materials.

Figure 8:
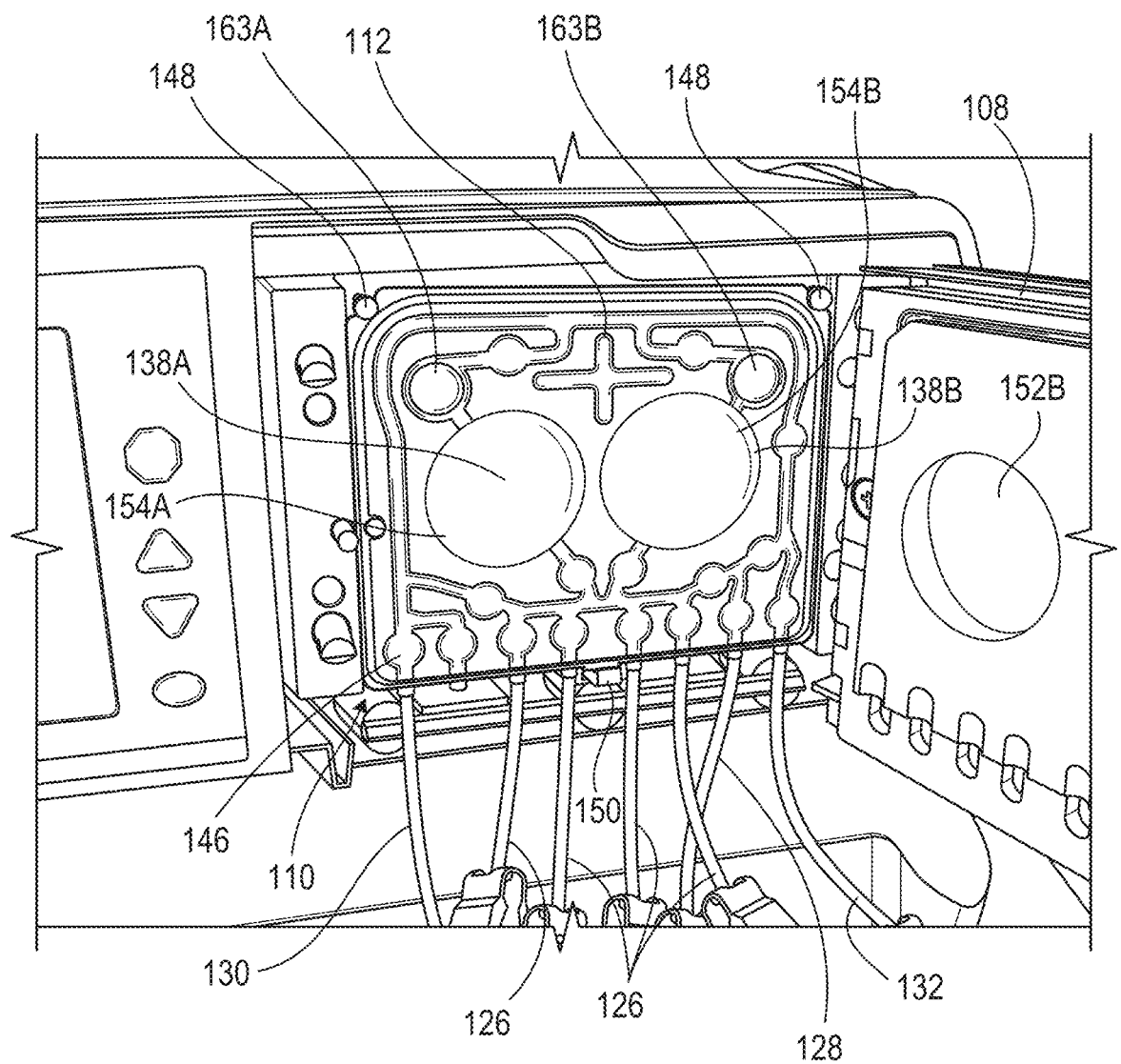
FIG. 8 is a perspective view of the PD cassette in the cassette compartment of the PD cycler of the PD system of FIG. 1.

As shown in FIG. 8, before treatment, the door 108 of the PD machine 102 is opened to expose the cassette interface 110, and the cassette 112 is positioned with its dome-shaped fastening members 161A, 161B aligned with the pistons 133A, 133B of the PD machine 102, its pressure sensing chambers 163A, 163B aligned with the pressure sensors 151A, 151B of the PD machine 102, its depressible dome regions 146 aligned with the inflatable members 142 of the PD machine 102, and its membrane 140 adjacent to the cassette interface 110. In order to ensure that the cassette 112 is properly positioned on the cassette interface 110, the cassette 112 is positioned between the locating pins 148 and the spring loaded latch 150 extending from the cassette interface 110. The asymmetrically positioned connectors 160 of the cassette act as a keying feature that reduces the likelihood that the cassette 112 will be installed with the membrane 140 and dome-shaped fastening members 161A, 161B facing in the wrong direction (e.g., facing outward toward the door 108). Additionally or alternatively, the locating pins 148 can be dimensioned to be less than the maximum protrusion of the projections 154A, 154B such that the cassette 112 cannot contact the locating pins 148 if the membrane 140 is facing outward toward the door 108. The pistons 133A, 133B are typically retracted into the piston access ports 136A, 136B during installation of the cassette 112 to avoid interference between pistons 133A, 133B and the dome-shaped fastening members 161A, 161B and thus increase the ease with which the cassette 112 can be positioned within the cassette compartment 114.

After positioning the cassette 112 as desired on the cassette interface 110, the door 108 is closed and the inflatable pad within the door 108 is inflated to compress the cassette 112 between the inflatable pad and the cassette interface 110. This compression of the cassette 112 holds the projections 154A, 154B of the cassette 112 in the recesses 152A, 152B of the door 108 and presses the membrane 140 tightly against the raised ridges 167 extending from the planar surface of the rigid base 156 to form the enclosed fluid pathways 158 and dome regions 146 (shown in FIG. 6). Referring briefly also to FIGS. 1 and 2, the patient line 130 is then connected to a patient's abdomen via a catheter, and the drain line 132 is connected to a drain or drain receptacle. In addition, the heater bag line 128 is connected to the heater bag 124, and the dialysate bag lines 126 are connected to the dialysate bags 122. At this point, the pistons 133A, 133B can be coupled to dome-shaped fastening members 161A, 161B of the cassette 112 to permit priming of the cassette 112 and the lines 126, 128, 130, 132. Once these components have been primed, treatment can be initiated.

FIGS. 9A-9G, which will be discussed below, are cross-sectional views of the system during different stages of the setup, priming, and treatment. These figures focus on the interaction between the piston 133A of the PD machine 102 and the pump chamber 138A of the cassette 112 during the setup, priming, and treatment. The interaction between the other piston 133B and pump chamber 138B is identical and thus will not be separately described in detail.

Figure 9A:
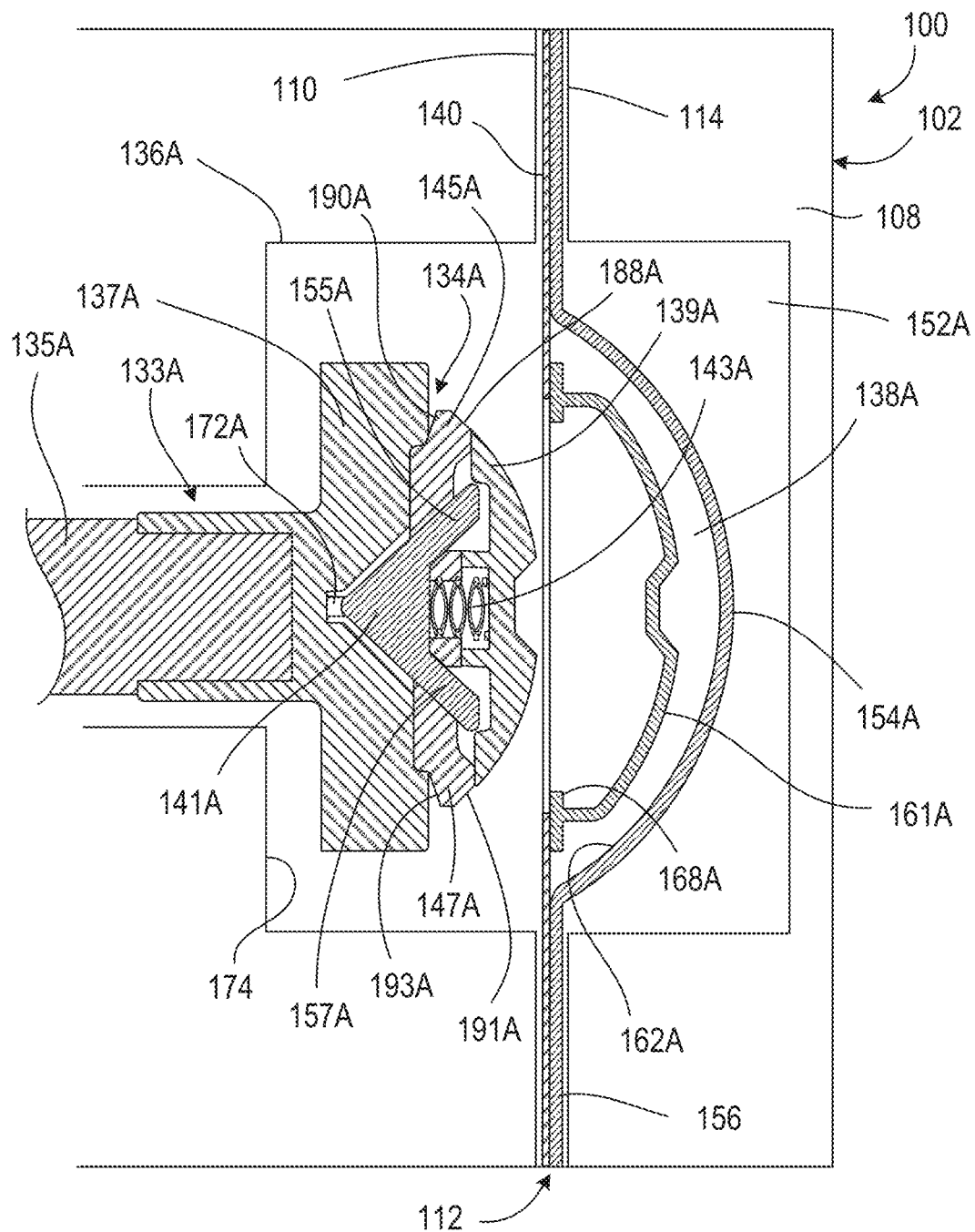
FIGS. 9A-9G are diagrammatic cross-sectional views of the PD system of FIG. 1 with the PD cassette disposed in the cassette compartment of the PD cycler, during different phases of a PD treatment and setup.

FIG. 9A shows the piston 133A fully retracted into the piston access port 136A of the cassette interface 110. The cassette 112 is positioned in the cassette compartment 114 of the PD machine 102 and the inflatable pad in the door 108 of the PD machine 102 is inflated such that the cassette 112 is pressed tightly against the cassette interface 110 of the PD machine 102, as explained above.

Figure 9B:
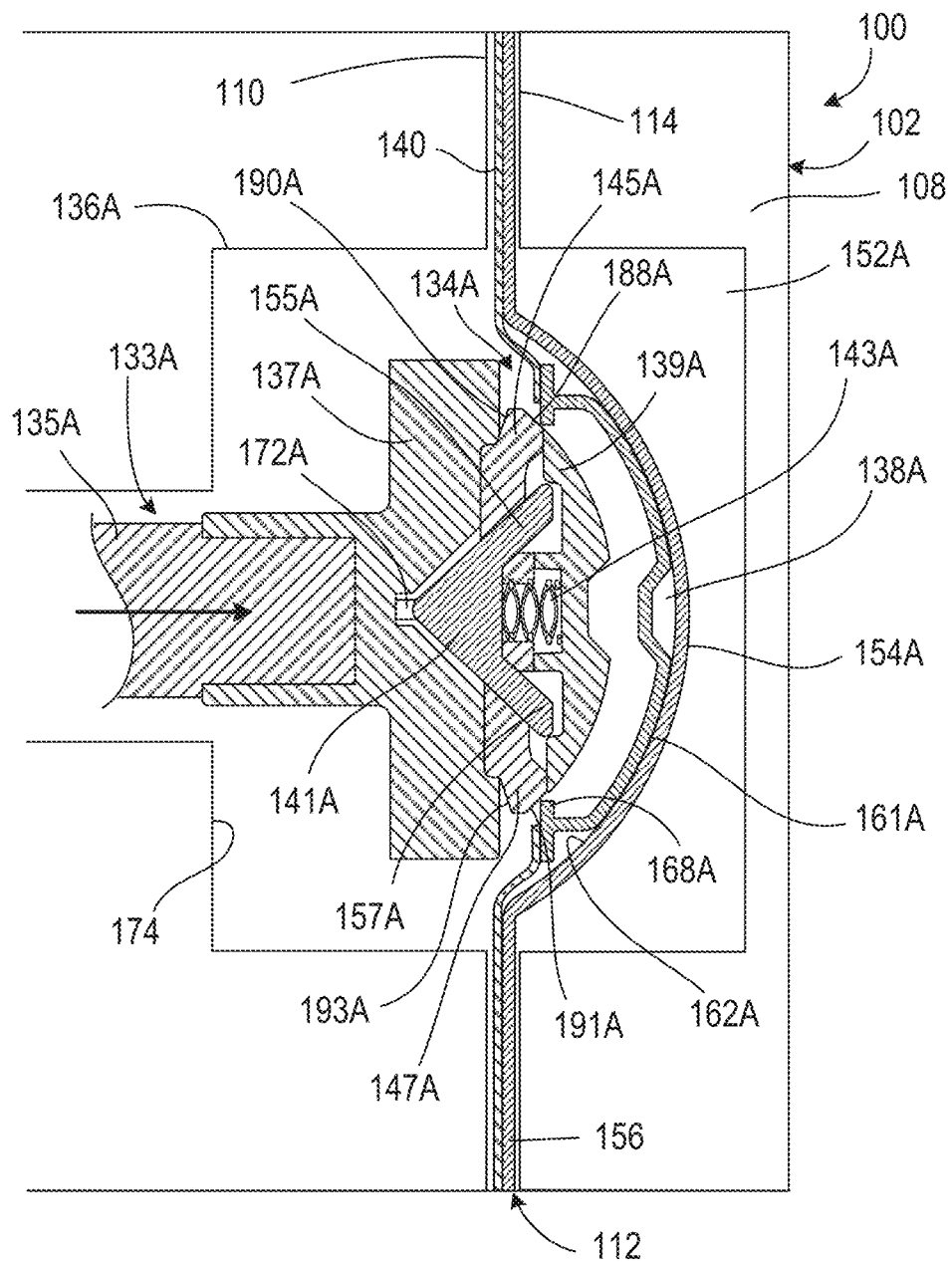

Referring to FIG. 9B, with the cassette 112 properly installed within the cassette compartment 114 of the PD machine 102 and the appropriate line connections made, the piston 133A is advanced to initiate the process of mechanically connecting the piston head 134A of the PD machine 102 to the dome-shaped fastening member 161A of the cassette 112. As the piston 133A is advanced, a front angled surface 188A of a sliding latch 145A and a front angled surface 191A of a sliding latch 147A contact a rear surface of the annular projection 168A, which extends radially inward from the dome-shaped fastening member 161A. The rear surface of the annular projection 168A is approximately perpendicular to the longitudinal axis of the piston 133A.

As the piston 133A continues to advance, the dome-shaped fastening member 161A contacts the inner surface of the portion of the rigid base 156 that forms the recessed region 162A, as shown in FIG. 9B. The rigid base 156 prevents further forward movement of the dome-shaped fastening member 161A. The membrane 140, which is attached to the peripheral flange 164A of the dome-shaped fastening member 161A, also stretches and moves into the recessed region 162A due to the advancing piston 133A. Due to the angled geometries of the front angled surfaces 188A, 191A of the sliding latches 145A, 147A and the resistance provided by the rigid base 156 to the forward motion of the dome-shaped fastening member 161A, the sliding latches 145A, 147A are caused to move radially inward (i.e., toward the longitudinal axis of the piston 133A) as the piston head 134A continues to be advanced relative to the dome-shaped fastening member 161A. More specifically, the forward motion of the sliding latches 145A, 147A is converted into a combined forward and radially inward motion due to the sliding motion of the front angled surfaces 188A, 191A of the sliding latches 145A, 147A against the rear surface of the annular projection 168A of the dome-shaped fastening member 161A. The radial inward movement of each of the sliding latches 145A, 147A in turn causes a forward movement of a latch lock 141A of the piston head 134A due to the mated geometries of the outer surfaces of legs 155A, 157A of the latch lock 141A and the surfaces of the sliding latches 145A, 147A that are positioned adjacent to and brought into contact with those outer surfaces of the legs 155A, 157A. This forward movement of the latch lock 141A is resisted by a spring 143A in the piston head.

Figure 9C:
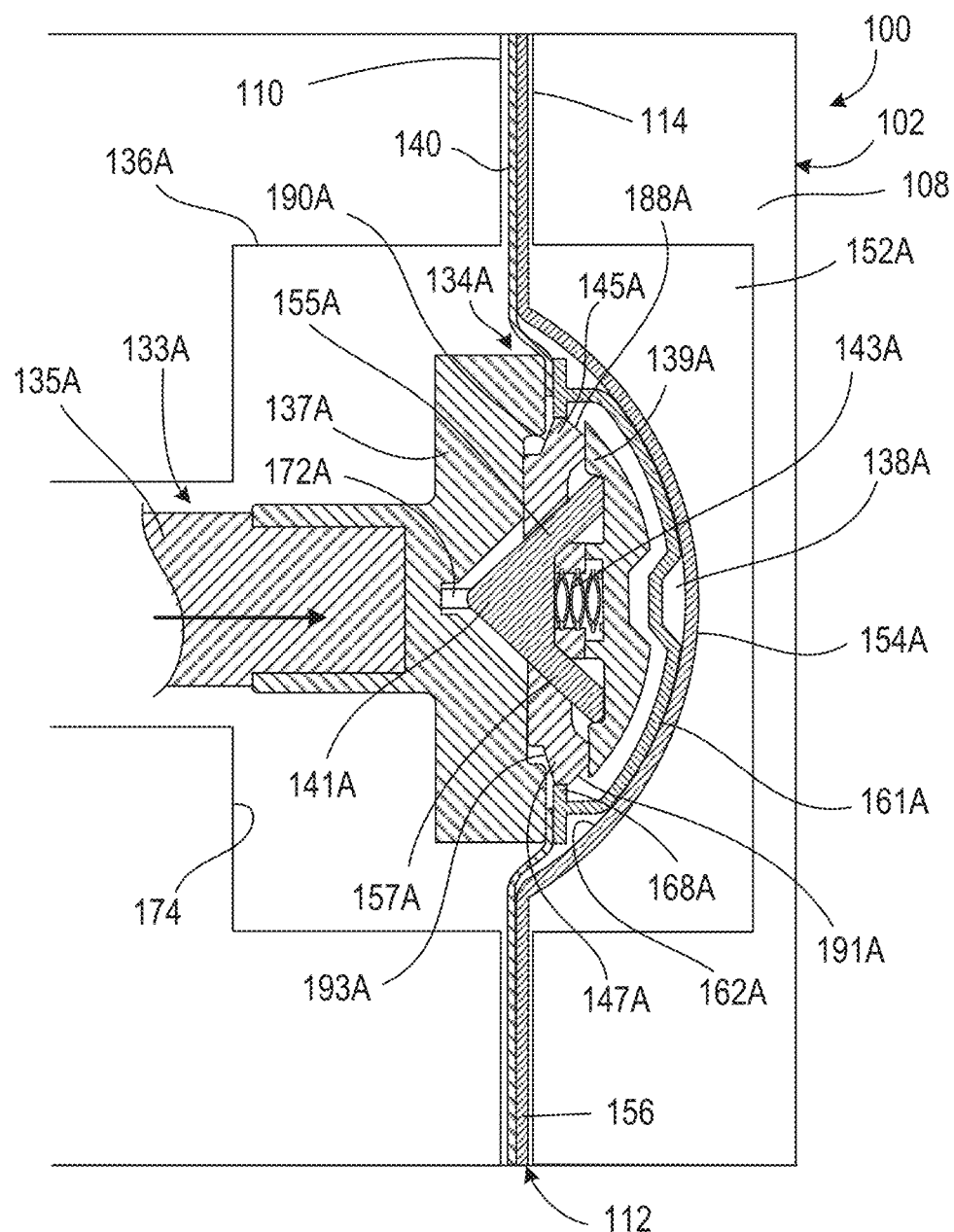

FIG. 9C shows the piston head 134A at a point during the connection process at which the sliding latches 145A, 147A have been deflected radially inward a sufficient distance to allow the sliding latches 145A, 147A to pass beyond the annular projection 168A that extends radially inward from the dome-shaped fastening member 161A. In this position, outer peripheral surfaces of the sliding latches 145A, 147A, which are substantially parallel to the longitudinal axis of the piston 133A, contact and slide along an inner surface of the annular projection 168A of the dome-shaped fastening member 161A, which is also substantially parallel to the longitudinal axis of the piston 133A. The spring 143A is further compressed due to the radially inwardly deflected positions of the sliding latches 145A, 147A.

Figure 9D:
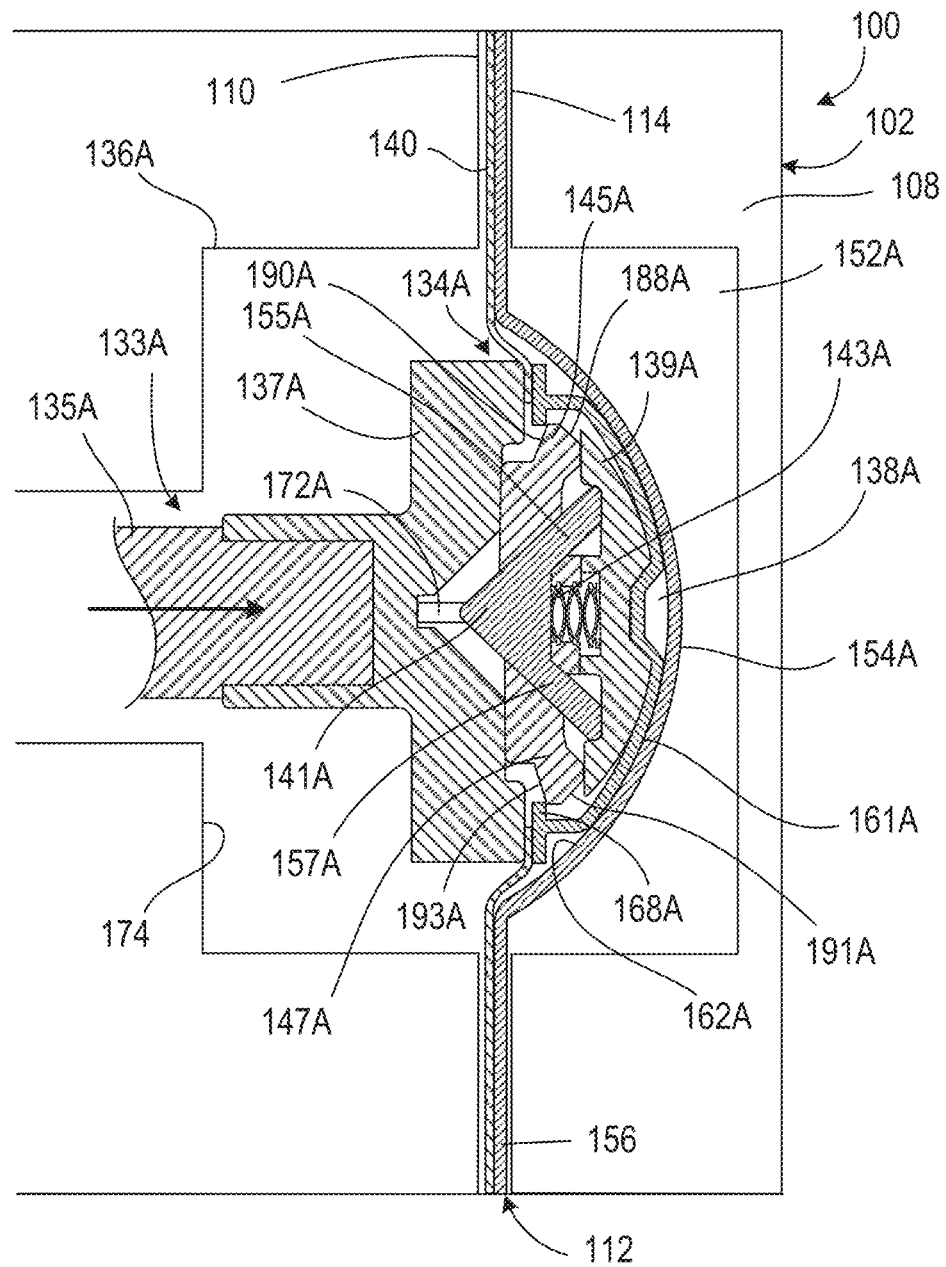

Referring to FIG. 9D, as the sliding latches 145A, 147A pass beyond the annular projection 168A, the spring 143A is allowed to expand. The expansion of the spring 143A causes the latch lock 141A to move rearward. As a result, the outer surfaces of the legs 155A, 157A of the latch lock 141A contact the correspondingly angled adjacent surfaces of the sliding latches 145A, 147A, causing the sliding latches 145A, 147A to move radially outward underneath the projection 168A of the dome-shaped fastening member 161A. Rear angled surfaces 190A, 193A of the sliding latches 145A, 147A ride along the front surface of the projection 168A of the dome-shaped fastening member 161A, which is slightly angled toward the rear of the dome-shaped fastening member 161A, as the sliding latches 145A, 147A move radially outward. The sliding latches 145A, 147A become wedged beneath the projection 168A as the sliding latches 145A, 147A move radially outward.

Figure 9E:
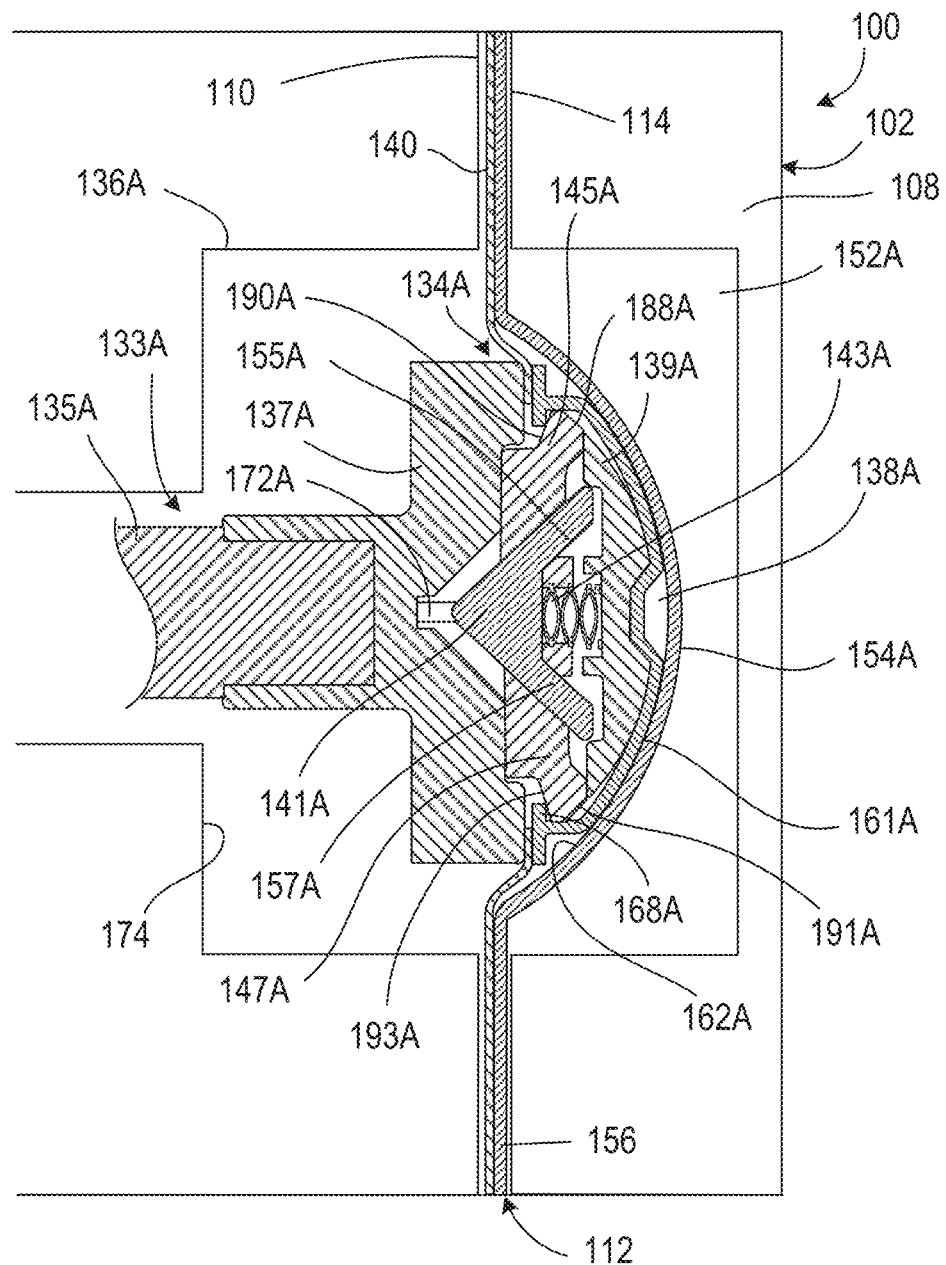

FIG. 9E illustrates the completed mechanical connection between the piston head 134A and the dome-shaped fastening member 161A in which the sliding latches 145A, 147A have moved to maximum outwardly displaced positions within the dome-shaped fastening member 161A. In this configuration, the projection 168A of the dome-shaped fastening member 161A is effectively pinched between a rear member 137A of the piston head 134A and the sliding latches 145A, 147A, resulting in a secure engagement between the piston head 134A and the dome-shaped fastening member 161A. As a result of the secure engagement of the piston head 134A to the dome-shaped fastening member 161A, the amount of slippage of the piston head 134A relative to the dome-shaped fastening member 161A can be reduced (e.g., minimized) and thus precise pumping can be achieved.

After mechanically coupling the piston head 134A of the PD machine 102 to the dome-shaped fastening member 161A of the cassette 112, a priming technique is carried out to remove air from the cassette 112 and from the various lines 126, 128, 130, 132 connected to the cassette 112. To prime the cassette 112 and the lines 126, 128, 130, 132, the piston 133A and inflatable members 142 are typically operated to pump dialysate from the heater bag 124 to the drain and from each of the dialysate bags 122 to the drain. Dialysate is also passed (e.g., by gravity) from the heater bag 124 to the patient line 130 to force any air trapped in the patient line out of a hydrophobic filter positioned at the distal end of the patient line 130.

Figure 9F:
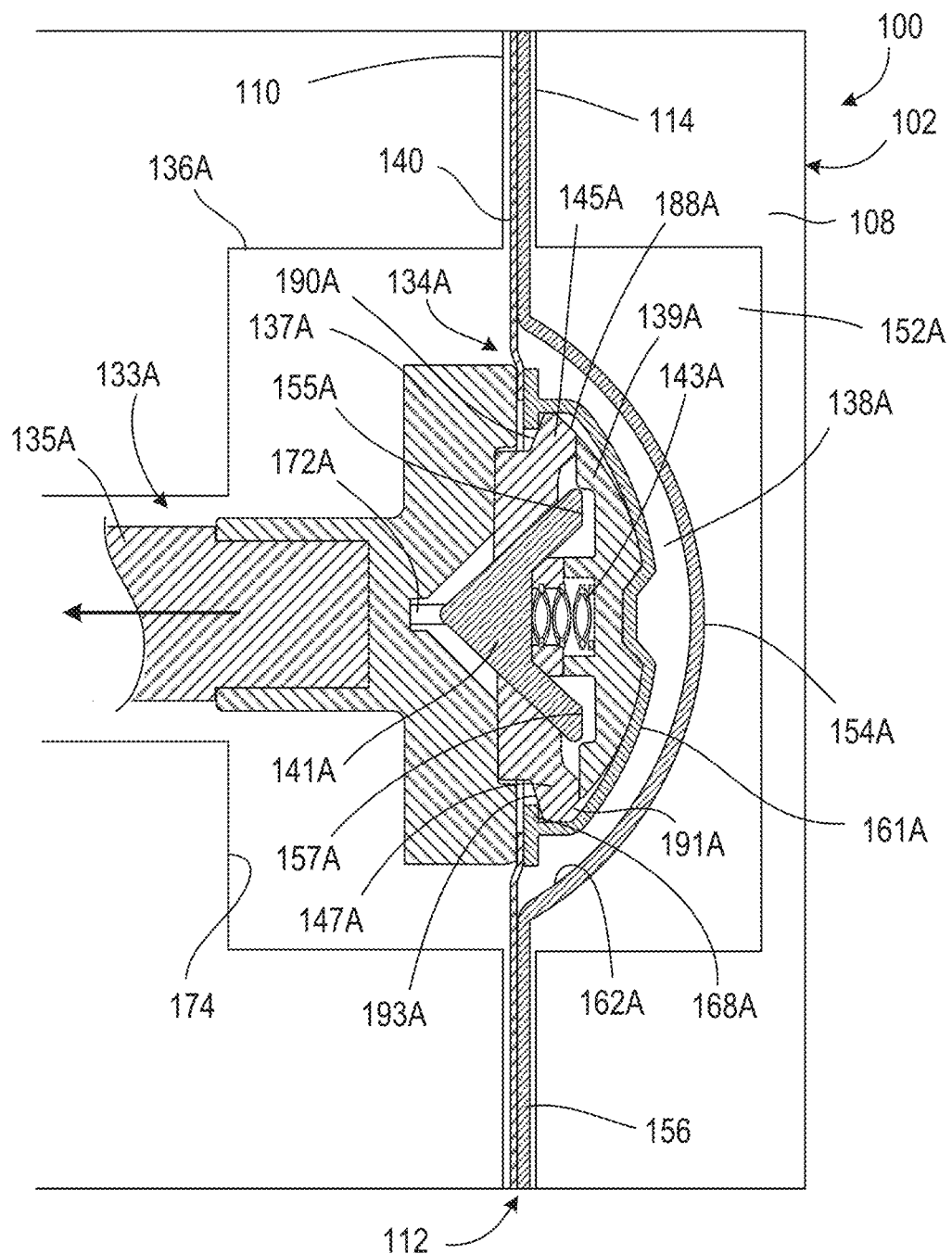

After priming is complete, the patient line 130 is connected to the patient and the PD machine 102 is operated to drain any spent dialysate that was left in the patient's peritoneal cavity from a previous treatment. To drain the spent dialysate from the patient's peritoneal cavity, the inflatable members 142 of the PD machine 102 are configured to create an open fluid flow path between the patient line 130 and the port 187A (shown in FIG. 4) of the pump chamber 138A, and the piston 133A is retracted to draw spent dialysate from the peritoneal cavity of the patient into the pump chamber 138A via the patient line 130, as shown in FIG. 9F. Because the piston head 134A is mechanically connected to the dome-shaped fastening member 161A and the dome-shaped fastening member 161A is attached to the membrane 140 of the cassette 112, the retraction of the piston 133A causes the dome-shaped fastening member 161A and the portion of the membrane 140 attached to the dome-shaped fastening member 161A to move rearwardly. As a result, the volume of the pump chamber 138A is increased and spent dialysate is drawn into the pump chamber 138A from the peritoneal cavity of the patient. The spent dialysate travels from the patient line 130 through the pressure sensing chamber 163A and then enters the pump chamber 138A via the port 187A. The pressure sensor 151A is able to monitor the pressure in the pressure sensing chamber 163A, which is approximately equal to the pressure in the pump chamber 138A, during this process.

Figure 9G:
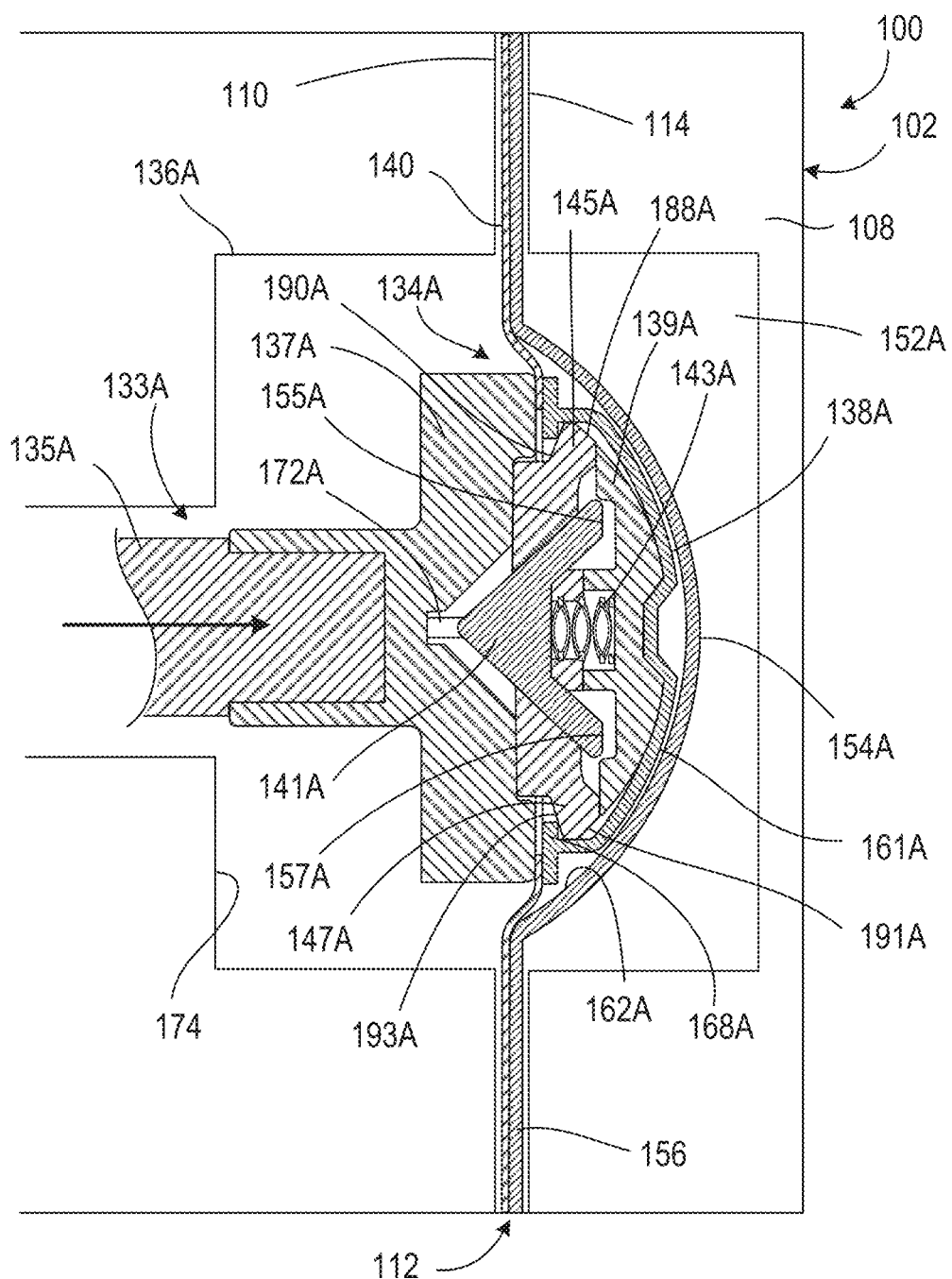

Referring to FIG. 9G, after drawing the dialysate into the pump chamber 138A from the peritoneal cavity of the patient, the inflatable members 142 are configured to create an open fluid flow path between the port 185A (shown in FIG. 4) of the pump chamber 138A and the drain line 132, and the dialysate is forced out of the pump chamber 138A to the drain by advancing the piston 133A and decreasing the volume of the pump chamber 138A. The piston 133A is typically advanced until the dome-shaped fastening member 161A contacts or nearly contacts the inner surface of the recessed region of the base 156 so that substantially all of the dialysate is forced out of the fluid pump chamber 138A via the port 185A.

During the patient drain phase of the treatment, the pistons 133A, 133B are typically alternately operated such that the piston 133A is retracted to draw spent dialysate solution into the pump chamber 138A from the patient while the piston 133B is advanced to pump spent dialysate solution from the pump chamber 138B to the drain and vice versa.

To begin the patient fill phase, the inflatable members 142 are configured to create a clear fluid flow path between the pump chamber 138A and the heater bag line 128, and then the piston 133A is retracted, as shown in FIG. 9F, to draw warm dialysate from the heater bag 124 to the pump chamber 138A. The warm dialysate travels from the heater bag 124 through the heater bag line 128 and into the pump chamber via the port 185A.

The warm dialysate is then delivered to the peritoneal cavity of the patient via the patient line 130 by configuring the inflatable members 142 to create a clear fluid flow path between the pump chamber 138A and the patient line 130 and advancing the piston 133A, as shown in FIG. 9G. The warm dialysate exits the pump chamber 138A via the port 187A and travels through the pressure sensing chamber 163A to the patient line 130 before reaching the peritoneal cavity of the patient. The pressure sensor 151A is able to monitor the pressure in the pressure sensing chamber 163A, which is approximately equal to the pressure in the pump chamber 138A, during this process.

During the patient fill phase of the treatment, the pistons 133A, 133B are typically alternately operated such that the piston 133A is retracted to draw warm dialysate into the pump chamber 138A from the heater bag 124 while the piston 133B is advanced to pump warm dialysate from the pump chamber 138B to the patient and vice versa. When the desired volume of dialysate has been pumped to the patient, the machine 102 transitions from the patient fill phase to a dwell phase during which the dialysate is allowed to sit within the peritoneal cavity of the patient for a long period of time.

During the dwell period, toxins cross the peritoneum of the patient into the dialysate from the patient's blood. As the dialysate dwells within the patient, the PD machine 102 prepares fresh dialysate for delivery to the patient in a subsequent cycle. In particular, the PD machine 102 pumps fresh dialysate from one of the four full dialysate bags 122 into the heater bag 124 for heating. To do this, the pump of the PD machine 102 is activated to cause the pistons 133A, 133B to reciprocate and certain inflatable members 142 of the PD machine 102 are inflated to cause the dialysate to be drawn into the fluid pump chambers 138A, 138B of the cassette 112 from the selected dialysate bag 122 via its associated line 126. The dialysate is then pumped from the fluid pump chambers 138A, 138B to the heater bag 124 via the heater bag line 128.

After the dialysate has dwelled within the patient for the desired period of time, the spent dialysate is pumped from the patient to the drain in the manner described above. The heated dialysate is then pumped from the heater bag 124 to the patient where it dwells for a desired period of time. These steps are repeated with the dialysate from two of the three remaining dialysate bags 122. The dialysate from the last dialysate bag 122 is typically delivered to the patient and left in the patient until the subsequent PD treatment.

After completion of the PD treatment, the pistons 133A, 133B are retracted in a manner to disconnect the piston heads 134A, 134B from the dome-shaped fastening members 161A, 161B of the cassette. The door 108 of the PD machine 102 is then opened and the cassette 112 is removed from the cassette compartment 114 and discarded.

Figure 10:
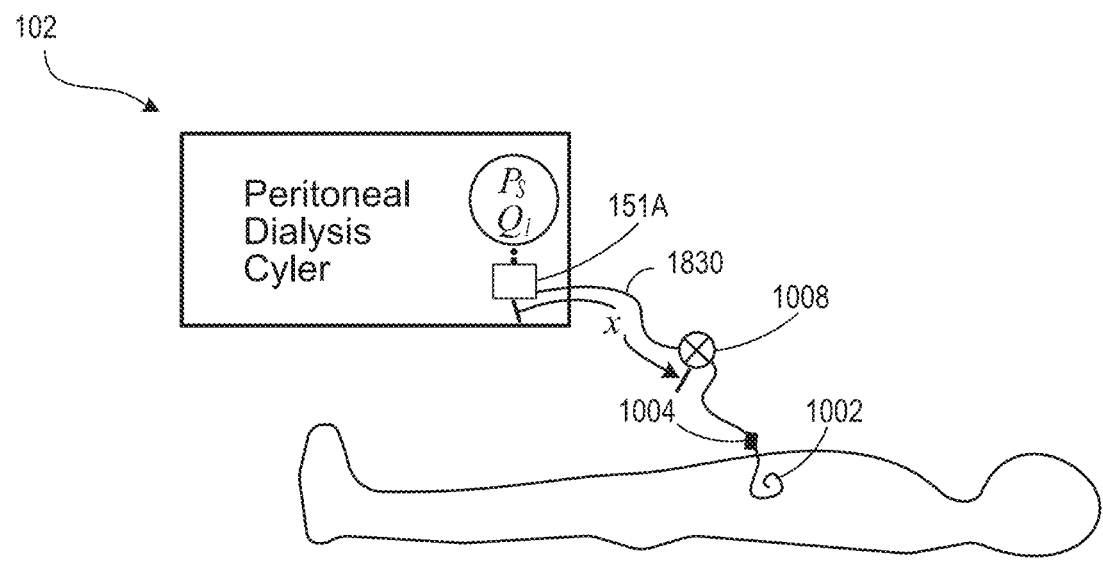
FIG. 10 shows a schematic diagram of the PD cycler of FIG. 1 connected to a patient with an occlusion present in the patient line.

FIG. 10 shows a schematic diagram of the PD machine 102 connected to a patient. A proximal end of the patient line 130 is connected to the PD machine 102 at a port (e.g., an inlet/outlet), and a distal end of the patient line 130 is connected to the patient's abdomen via the catheter 1002. The catheter 1002 is connected to the patient line via a port 1004. The patient line 130 may be a tube made of a distensible and/or flexible material that is at least partially distended by operating pressures in the PD machine 102. For example, the patient line 130 may be made of an elastomeric material such as a polymer that develops a swell in response to positive operating pressures in the PD machine 102. The patient line 130, the port 1004, and the catheter 1002 are sometimes referred to herein as the patient line-catheter conduit, or simply the conduit. One of the pressure sensors 151A is located at the proximal end of the patient line 130 (e.g., at the end of the patient line 130 that is nearest to the PD machine 102). The pressure sensor 151A is configured to measure the pressure in the patient line 130. In some implementations, the pressure sensor 151A include a transducer that generates a signal as a function of the pressure imposed. The signal is indicative of the magnitude and sign of the measured pressure.

During a PD treatment cycle, an occlusion can occur at different locations in the conduit. For example, the patient line 130 may become kinked or pinched, holes in the catheter 1002 may become occluded (e.g., with omental fat), or the patient line 130 may develop an internal blockage at some location (e.g., from a deposit of omental fat). The PD machine 102 is configured to adjust its operation in response to an occlusion being detected. For example, the control unit 139 may be configured to adjust one or more operating parameters of the PD machine 102 in an attempt to clear the occlusion and/or to modulate the flow in the patient line to avoid an overpressure condition. In some implementations, the control unit 139 may be configured to provide an alert indicating that an occlusion has been detected. For example, a visual, tactile, and/or audible alert may be directed to the patient (e.g., to wake the patient).

In order to determine an appropriate response, the PD machine 102 is configured to ascertain the type of occlusion that is present. In some implementations, the type of occlusion can be inferred based on the location of the occlusion in the conduit. For example, if an occlusion is detected in the catheter 1002, the PD machine 102 can infer that holes in the catheter 1002 may be occluded. Similarly, if the occlusion is detected somewhere along the patient line 130, the PD machine 102 can infer that the patient line 130 is kinked or pinched. The PD machine 102 is configured to determine a location of the occlusion relative to the position of the pressure sensor 151A. The particular location of the occlusion can be considered by the PD machine 102 to determine the appropriate response. In the example shown in FIG. 10, an occlusion 1008 is present in the patient line 130 at a distance x from the patient line port and/or the pressure sensor 151A, which may be indicative of a kink or a pinch in the patient line 130.

During the treatment, solution is exchanged (e.g., transferred, conveyed, etc.) through the patient line 130. When the PD solution (e.g., the dialysate) being provided to or withdrawn from the patient line 130 encounters an occlusion, the patient line 130 may develop a deformity. For example, in the case of the solution being pumped toward the patient (e.g., solution being injected), the elastic material of the patient line 130 may expand in response to the solution encountering the occlusion, thereby resulting in an increase in volume and pressure within the patient line 130. In the case of the solution being pumped from the patient (e.g., solution being withdrawn), the elastic material of the patient line 130 may contract, thereby resulting in a decrease in volume and pressure within the patient line 130. The distensibility of the non-occluded portion of the conduit (e.g., the portion of the conduit between the patient line port and the occlusion 1008, sometimes referred to as the first portion) can be measured, and the location of the occlusion 1008 can be inferred from the measured value. The occlusion 1008 may define a boundary between the first portion of the conduit and a second portion of the conduit (e.g., the rest of the conduit). It is possible to infer the location of the occlusion 1008 because the distensibility itself arises from, among other things, the length of the non-occluded portion of the conduit 1008 (e.g., the distance x between the patient line port and the occlusion 1008).

The portion of the conduit between the patient line port and the occlusion 1008 is sometimes referred to as the non-occluded portion of the conduit or the pressurized portion of the conduit. The length of the pressurized portion of the conduit—the distance x between the patient line port and the occlusion 1008—can be determined by approximating the conduit as a thin-walled cylindrical pressure vessel. According to such an approximation, the normal stresses in the wall of the conduit are given according to Equations 1 and 2:

$$\sigma_\theta = \frac{P_g D}{2w} \quad (1)$$

$$\sigma_z = \frac{P_g D}{4w} \quad (2)$$

where $\sigma_\theta$ is the azimuthal (e.g., "hoop") stress, $\sigma_z$ is the longitudinal stress, $P_g$ is the transmural pressure experienced by the conduit (e.g., the gauge pressure of the fluid inside the conduit when the conduit's exterior is exposed to atmospheric pressure), D is the conduit's inner diameter, and w is the conduit's wall thickness. In some implementations (e.g. in implementations in which the conduit has a relatively thick wall), determining the stress state in the conduit may require other consideration in addition to the biaxial stress shown in Equations 1 and 2.

When a closed volume of tubing of the patient line 130 that is initially filled with a solution has an incremental volume $\Delta V_f$ of solution added while the occlusion 1008 is present, a change in pressure $\Delta P$ (e.g., a pressure rise) results. The magnitude of the change in pressure $\Delta P$ depends on the dimensions and the distensibility of the non-occluded portion of the patient line 130. If the change in pressure $\Delta P$, the incremental volume $\Delta V_f$, the properties related to the distensibility of the patient line 130, and some of the dimensions of the patient line 130 are known, the location of the occlusion 1008 (e.g., the distance x between the patient line port and the occlusion 1008) can be inferred. The incremental volume $\Delta V_f$ of added solution as a function of the change in pressure $\Delta P$ is given according to Equation 3:

$$\frac{\Delta V_f}{V_{f,i}} = 2a + 1.313a^2 + 0.281a^3 \quad (3)$$

where $V_{f,i}$ is the initial volume of the non-occluded portion of the patient line 130

$$a = \frac{D \Delta P}{E_y w},$$

and $E_y$ is the Young's modulus of the material of the patient line 130 (e.g., the Young's modulus of the elastomer). Equation 3 may assume that the Poisson ratio of the elastomer is 0.5, which may be a typical value for a rubber material. Equation 3 is derived from the stress tensor given by Equations 1 and 2, and may assume that the tubing material is isotropic with linear elastic properties.

Equation 3 implies that for a given incremental volume $\Delta V_f$ of injected solution, the resulting rise in pressure $\Delta P$ depends upon the initial volume of the pressurized region $V_{f,i}$. For conditions where $a \ll 1$ (e.g., small strain approximation), $\Delta P$ is proportional to $$\frac{\Delta V_f}{\Delta V_{f,i}}.$$

Such a condition is expect to be maintained. In a conservative example (e.g., for soft rubber having $E_y \approx 0.01$ gigapascals), a relatively high $\Delta P$ of 600 mbar and representative tubing dimensions of D=4 mm and w=1 mm may yield a=0.024. Thus, under the expected conditions, Equation 3 can be approximated by Equation 4:

$$\frac{\Delta V_f}{V_{f,i}} = 2 \frac{D \Delta P}{E_y w} \quad (4)$$

and Equation 4 can be rearranged to yield Equation 5:

$$\Delta P = \frac{\Delta V_f}{C_f} \quad (5)$$

where the fluidic capacitance $C_f$ of the pressurized region of the patient line 130 is given by Equation 6:

$$C_f = 2 \frac{V_{f,i} D}{E_y w} \approx \frac{0.5\pi}{E_y} \frac{D^3}{w} x \quad (6)$$

In Equation 6, as in FIG. 10, x represents the distance (e.g., the length of tubing) between the patient line port and the occlusion 1008. The occlusion 1008 may be a complete or nearly-complete occlusion. The other factors of Equation 6 are relatively constant for a given sample of uniform tubing. Equation 6 illustrates that a measure of the fluidic capacitance $C_f$ can be translated into a measurement of the distance x between the patient line port and the occlusion 1008. The fluidic capacitance $C_f$ can be measured according to Equation 5 using existing components (e.g., the pressure sensor 151A) of the PD machine 102, and the distance x can then be determined according to Equation 6. In this way, the methods and techniques described herein can easily be implemented in existing systems. In some implementations, the relationship between the fluidic capacitance $C_f$ and the distance x between the patient line port and the occlusion 1008 can be evaluated empirically (e.g., rather than by direct use of Equation 6).

Figure 11:
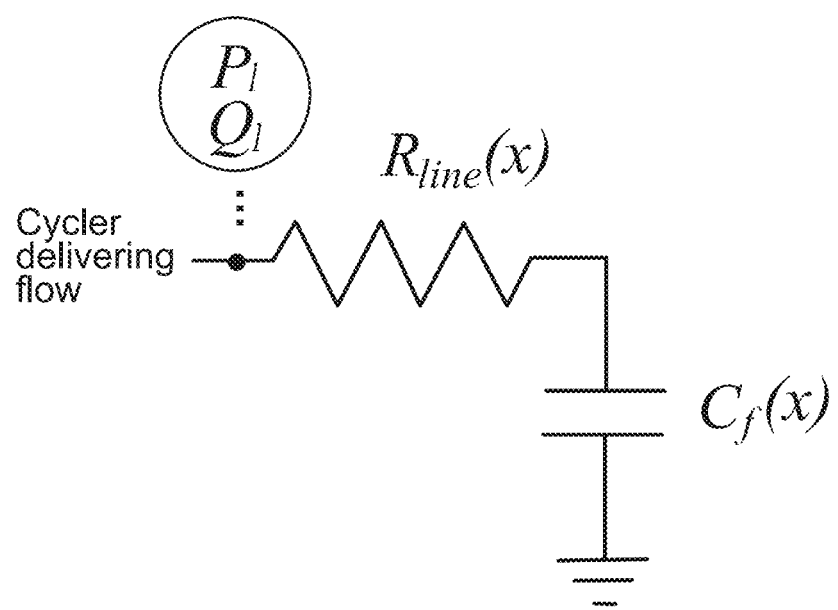
FIG. 11 shows a representation of a lumped-element electrical circuit analogous to the fluidic system of FIG. 10 for the case in which the occlusion creates a complete blockage of flow.

To help illustrate the method of measuring the fluidic capacitance $C_f$ of the pressurized region of the patient line 130, FIG. 11 shows a representation of a lumped-element electrical circuit that may be analogous to the fluidic system shown in FIG. 10 for the case of complete flow blockage. For the case of a partial flow blockage, the lumped-element electrical circuit may look similar to the representation shown in FIG. 19, with the second resistor representing $R_{blockage} + R_{downstream}$ (e.g., rather than $R_{catheter}$). The measurement of capacitance in the illustrated circuit may be performed by adding a known charge to the capacitor and measuring the resultant change in potential at the patient line port (e.g., position "1"). As described above, the equivalent fluidic measurement to adding a known charge is to inject a known incremental volume of solution, $\Delta V_f$, into the patient line 130 and measure the change in pressure $\Delta P$.

In reality, the illustrated resistance and capacitance of the patient line 130 are distributed throughout the length of the patient line 130 (e.g., rather than lumped into discrete elements). This fact in addition to other effects (e.g., such as elastic waves and strain-rate-sensitive elastic properties of the patient line 130) may give rise to transient behavior in the pressure in the patient line 130 after injecting the incremental volume of solution $\Delta V_f$. In some examples, measuring the change in pressure $\Delta P$ after such transients have subsided may lead to a more accurate measurement of the fluidic capacitance $C_f$.

Experiment 1

Figure 12:
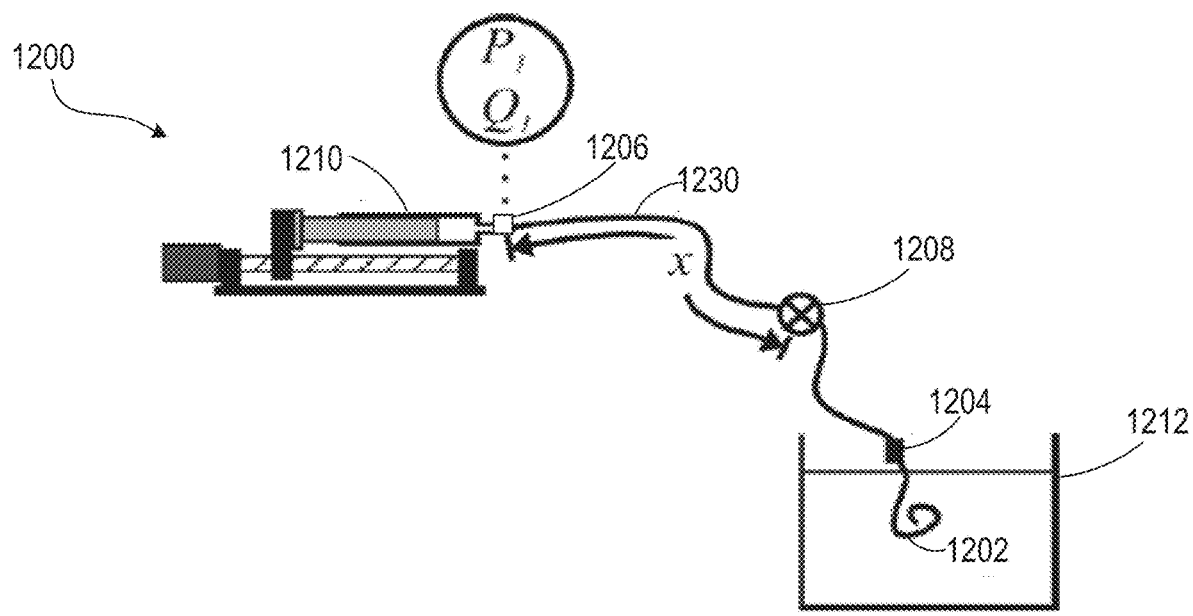
FIG. 12 shows an example experimental system for determining a fluidic capacitance $C_f$ of a pressurized region of a conduit.

FIG. 12 shows an example experimental system 1200 in which the fluidic capacitance $C_f$ of a pressurized region of a conduit can be determined. The system 1200 includes a syringe pump 1210 that is configured to inject a known incremental volume of fluid $\Delta V_f$ into the conduit that includes a tube 1230 (e.g., which mimics a patient line) and a catheter 1202 connected to the tube 1230 via a port 1204. In this example, the tube 1230 had a length of approximately ten feet and the syringe pump 1210 was driven by a programmable stepper motor. The catheter 1202 is submerged in a reservoir of fluid 1212 (e.g., in place of a patient). An occlusion 1208 is present in the tube 1230 at various distances x from a pressure sensor 1206 that is positioned at a proximal end of the tube 1230. In this example, the occlusion was created by hemostat clamping the tube 1230 at various distances x. The clamping of the tube 1230 represents a complete occlusion.

A relatively small known volume of distilled water (e.g., $\Delta V_f$ of approximately 0.33 cubic centimeters) was injected by the syringe pump 1210. The pressure sensor 1206 was configured to measure the pressure in the tube 1230 at the proximal end of the tube 1230 over time. The pressure measurements were made before, during, and after the injection. In some implementations, the pressure measurements occurred at a frequency in the order of hundreds of hertz or thousands of hertz (e.g., 1-2 kHz).

Figure 13:
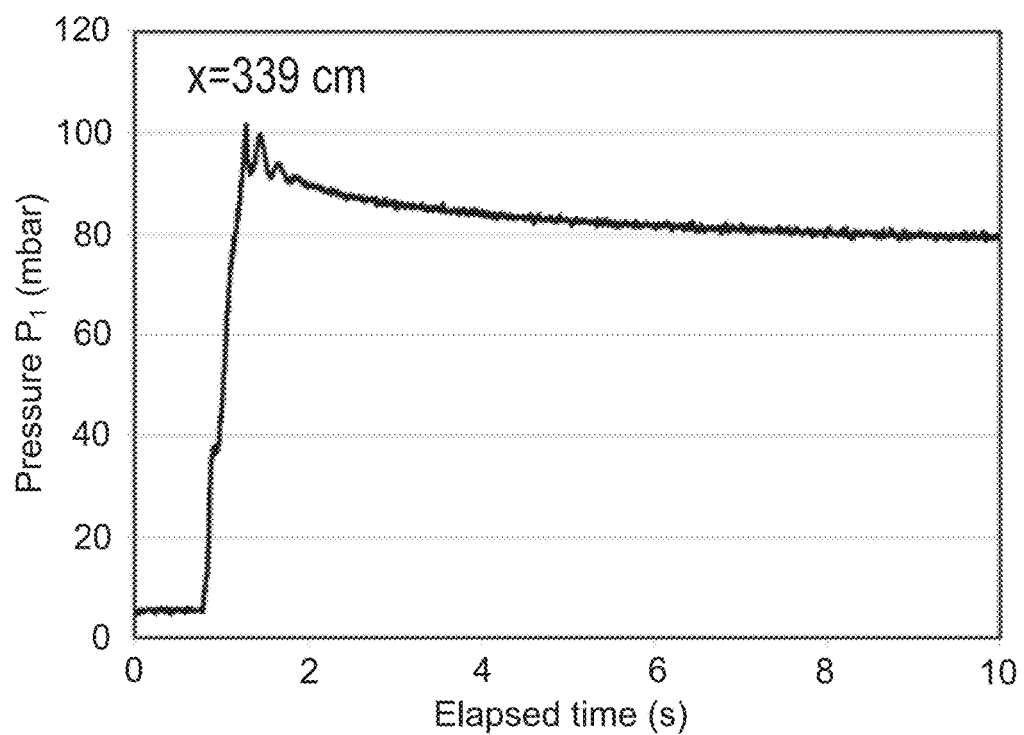
FIG. 13 shows a representative graph of pressures over time as measured by a pressure sensor of the system of FIG. 12.

FIG. 13 shows a representative graph of the pressure measurements P (in mbar) obtained by the pressure sensor 1206 over time (in seconds) when the occlusion 1208 was positioned at x=339 cm. The change in pressure $\Delta P$ was measured as the net change in pressure after the transient behavior had subsided. In this example, the change in pressure $\Delta P$ was approximately 75 mbar. With the incremental volume of injected fluid $\Delta V_f$ and the change in pressure $\Delta P$ being known, the fluidic capacitance $C_f$ was then determined according to Equation 5. In this example, the fluidic capacitance $C_f$ was determined to be approximately 4.4 cc/bar.

Figure 14:
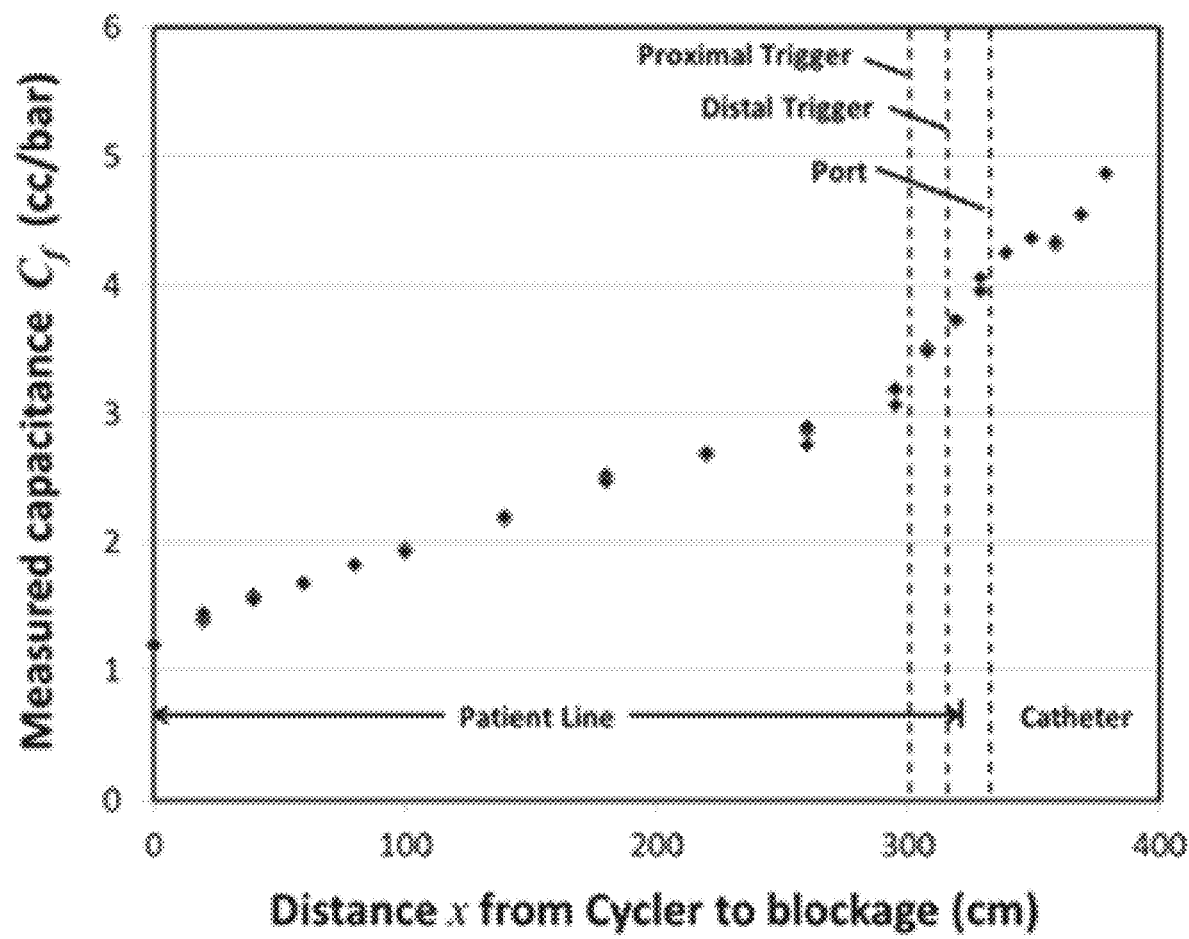
FIG. 14 shows a representative graph of calculated fluidic capacitances $C_f$ versus various clamping distances.

The experiment was then repeated for each of the tested distances x of the occlusion 1208. FIG. 14 shows a representative graph of the calculated fluidic capacitances $C_f$ (in cc/bar) versus the various distances x of the clampings (in centimeters). The data shown in FIG. 14 represents a "calibration curve" for fluidic capacitance $C_f$ versus the distance x to the occlusion in the particular system. The data show that fluidic capacitance $C_f$ correlates linearly with the distance x. The information can be used to refine the determination of the location of the occlusion. That is, using the fluidic capacitances $C_f$ determined according to Equation 5, Equation 6 may indicate that the corresponding occlusions are present at a particular distances x. But in this example, we know the actual distance x to the occlusions. Thus, errors between the calculated distances x and the actual distances x can be noted and considered for future determinations (e.g., for experiments in which the actual distance x of the occlusion is unknown).

While Experiment 1 has largely been described in terms of a "fill direction" implementation in which an incremental volume $\Delta V_f$ of solution is provided to (e.g., dispensed into) the conduit, thereby resulting in a pressure increase, the same principles and equations apply to "drain direction" implementations in which solution is withdrawn from the conduit, thereby resulting in a pressure decrease in the conduit.

Experiment 2

Experiment 1 was used to corroborate the validity of Equations 1-6 and to determine a calibration curve for the experimental system 1200 of FIG. 12 testing for complete occlusions. Experiment 2 studies a similar technique implemented in an actual dialysis machine (e.g., the PD machine 102 of FIGS. 1-10) using the built-in pressure sensor 151A to test for partial occlusions. The advanced testing described below was performed to achieve results that are more relevant to real PD treatment.

The experiment primarily focused on flow in the drain direction. The choice to focus on flow in the drain direction was made for the following reasons: i) a majority of problematic blockages typically occur in the drain direction; ii) a greater potential for difficulty was predicted in the drain direction due to possible pull-off of cassette film from the pump; and iii) initial tests in the fill direction suggested that the same patterns of pressure versus flow should be obtainable—albeit with different calibration curves that would need to be empirically determined.

Figure 15:
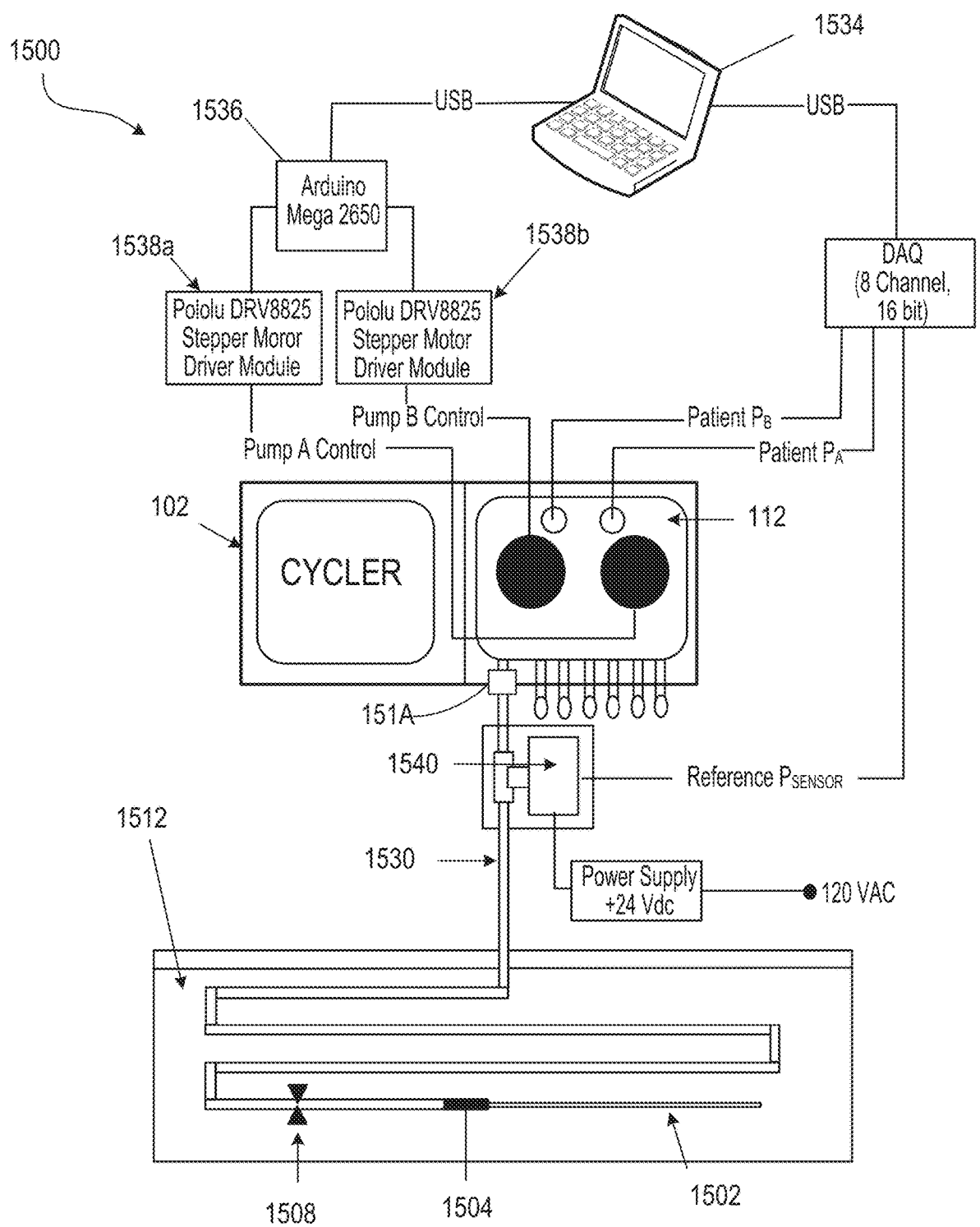
FIG. 15 shows a schematic of a dialysis system that includes components for flow control and pressure measurement.

FIG. 15 shows a schematic of a dialysis system 1500 in which the fluidic capacitance $C_f$ of a pressurized region of a conduit can be determined. The dialysis system 1500 includes added components for flow control and pressure measurement used in the validation experiments described herein. For example, the dialysis system 1500 includes additional components that may not typically be included in a dialysis system for ordinary use with a patient.

The dialysis system 1500 includes the PD machine 102, the PD cassette 112 housed in the PD machine 102, a patient line 1530, and the pressure sensor 151A located at a proximal end of the patient line 1530. The patient line 1530 may be substantially similar to the patient line 130 described above with respect to FIGS. 1 and 10. In some implementations, the patient line 1530 may be a 10-foot patient line with dual patient connectors. In this example, the PD machine 102 is controlled by a computing device 1534 and a microcontroller 1536 such as a Mega 2650 microcontroller manufactured by Arduino LLC. In some implementations, the PD machine 102 may be controlled by a control unit (e.g., a processor) of the PD machine 102, such as the control unit 139 shown in FIG. 1. The microcontroller 1536 is operatively coupled to driver modules 1538a, 1538b. The driver modules 1538a, 1538b may be DRV8825 stepper motor driver modules manufactured by Pololu Corporation.

The microcontroller 1536, at the direction of code executed by the computing device 1534, is configured to control the driver modules 1538a, 1538b to cause the driver modules 1538a, 1538b to operate pumps of the PD machine 102 (e.g., the pistons 133A, 133B of FIG. 2) in order to impose specified flow patterns. The microcontroller 1536 and the driver modules 1538a, 1538b provided pulse streams to the pumps to accomplish the following types of motion: i) return to the "home" position as defined by an onboard limit switch; ii) move forward by a specified number of steps, in a user-defined stepping mode from full stepping to various increments of microstepping; and iii) move backward by a specified number of steps in a user-defined stepping mode. Some flow patterns were determined to be more desirable than others for the purpose of occlusion detection. Such desirable flow patterns were programmed in a sequence that is described below.

The ability to detect a partial occlusion (e.g., as compared to detecting a complete occlusion) presents challenges that do not manifest when detecting a complete occlusion. Typically, the less restrictive an occlusion is, the greater is the challenge for sensitivity and specificity of a method for determining its location. A relevant standard for quantifying partial occlusions in the PD machine 102 comes from the Drain Complication and Fill Complication conditions. Drain Complication and Fill Complication conditions occur when there is a flow restriction sufficient to depress the flow below a threshold value for a particular period of time. In a model case of a steady-state flow restriction, the threshold value of restriction that would generate a Drain Complication is one that would require a pressure of approximately −200 mbar (as measured at the pressure sensor 151A) to drive a flow of approximately 30 milliliters per minute.

The pumps are configured to cause fluid to be pumped through a patient line-catheter conduit that includes the patient line 1530, a catheter 1502, and a port 1504 that connects the patient line 1530 to the catheter 1502. The catheter 1502 may be a Flex Neck Classic catheter. The catheter 1502, the port 1504, and a portion of the patient line 1530 is submerged in a basin of water 1512 (e.g., in place of a patient). The water was held at room temperature (e.g., 20-25° C.). The free surface of the water was kept at the same height (e.g., ±2 centimeters) with respect to the direction of gravity as that of the pressure sensor 151A of the PD cycler 102. An occlusion 1508 was provided in the patient line 1530 at various distances x from the pressure sensor 151A, with the occlusion 1508 defining a boundary between a first portion of the conduit (e.g., the pressured portion) and a second portion of the conduit (e.g., the rest of the conduit). The occlusions 1508 represented partial occlusions.

The distance x to the occlusions 1508 can be inferred from a measurement of the fluidic capacitance $C_f$ of the pressurized region of a conduit (e.g., the segment of the patient line 1530 between the PD cycler 102 and the occlusion 1508). For a patient line 1530 with tubing of uniform mechanical properties and cross-sectional dimensions (e.g., which is largely true in practice), the fluidic capacitance $C_f$ is related proportionately to the length of tubing comprising the "capacitor." The so-called capacitor can be "charged" by adding or withdrawing fluid at a fixed rate of flow, in a time interval short compared to the characteristic time of fluidic "leakage" through the partial occlusion. The fluidic capacitance $C_f$ may then be measured by its definition as the slope of distended volume versus pressure. In other words, two or more pressure measurements can be made during the withdrawing or dispensing stroke, the slope of the pressure versus time plot can be determined, and the distance x to the occlusions 1508 can be determined.

Equation 6 presents the theoretical basis by which the fluidic capacitance $C_f$ is expected to be proportional to the distance x to the occlusion, with the constant of proportionality being a function only of tubing properties and cross-sectional dimensions. Equation 5 can be rearranged to present the differential definition of the fluid capacitance $C_f$, as shown in Equation 7:

$$C_f = \frac{dV}{dP} \tag{7}$$

During "charging" of a capacitor by the action of a fixed rate dV/dt of fluid injection or removal, the fluidic capacitance $C_f$ can be determined according to Equation 8:

$$C_f = \frac{\frac{dV}{dt}}{\frac{dP}{dt}} \tag{8}$$

As was the case in Experiment 1, once the fluidic capacitance $C_f$ of the pressurized region of the patient line 130 is calculated, the distance x to the occlusion can be determined according to Equation 6.

Experiment 2 included the following general steps, which were performed for occlusions at various different distances:
  i. use the pump to add (for Fill Direction testing) or withdraw (for Drain Direction testing) a short burst (e.g., a "short stroke") of flow at a fixed and known volumetric flow rate;
  ii. detect and measure the rate of change of pressure versus time at the pressure sensor 151A; the time interval of data producing the slope estimate may be short compared to the characteristic decay time of the pressure;
  iii. calculate the effective fluidic capacitance $C_f$ using Equations 6-8; and
  iv. empirically determine a calibration curve between fluidic capacitance $C_f$ and distance x to the occlusion.

The experiment was performed at various distances x and across a large number of cassettes, with different types, degrees, and locations of flow restriction (e.g., occlusions), in order to investigate the potential sensitivity and specificity of the detection method. Sensitivity and specificity are statistical measures of the performance of the detection method. The sensitivity, also referred to as the true positive rate, measures the proportion of positives that are correctly identified as such. In this context, the sensitivity may correspond to the ability of the system to correctly identify occlusions (e.g., for distances x within a particular range). The specificity, also referred to as the true negative rate, measures the proportion of negatives that are correctly identified as such. In this context, the specificity may correspond to the accuracy of the detection method (e.g., the margin of error of determined distances x).

A small volume (e.g., approximately 0.33 cubic centimeters) of water was moved through the patient line 1530 in the drain direction by a first pump of the PD machine 102 (e.g., a pump controlled by a first one of the driver modules 1538a) at a fixed rate (e.g., 4.4 cubic centimeters per second). During this stroke, the pressure sensor 151A, which is built into the PD machine 102 and located at the proximal end of the patient line 1530, was used to measure two or more pressure values and detect the slope of pressure versus time for use in Equation 8.

The pressures were initially measured using both the pressure sensor 151A of the PD machine 102 and a reference pressure transducer 1540 positioned downstream from the pressure sensor 151A. The separate pressure measurements were taken to ensure that the pressure sensor 151A built into the PD machine 102 was capable of achieving the necessary. For example, the pressure sensor 151A is configured to detect the pressure in the patient line 1530 through a membrane of the cassette 112, and various fluidic elements are positioned between the pressure sensor 151A and the proximal end of the patient line 1530. It was considered that these elements may have the potential to diminish and/or distort the accuracy of the pressure measurements. Thus, measurements made by the reference pressure transducer 1540 were used to verify the fidelity of the measurements made by the pressure sensor 151A. A high degree of fidelity was observed, and the reference pressure transducer 1540 was removed to avoid possible artifacts.

Figure 16:
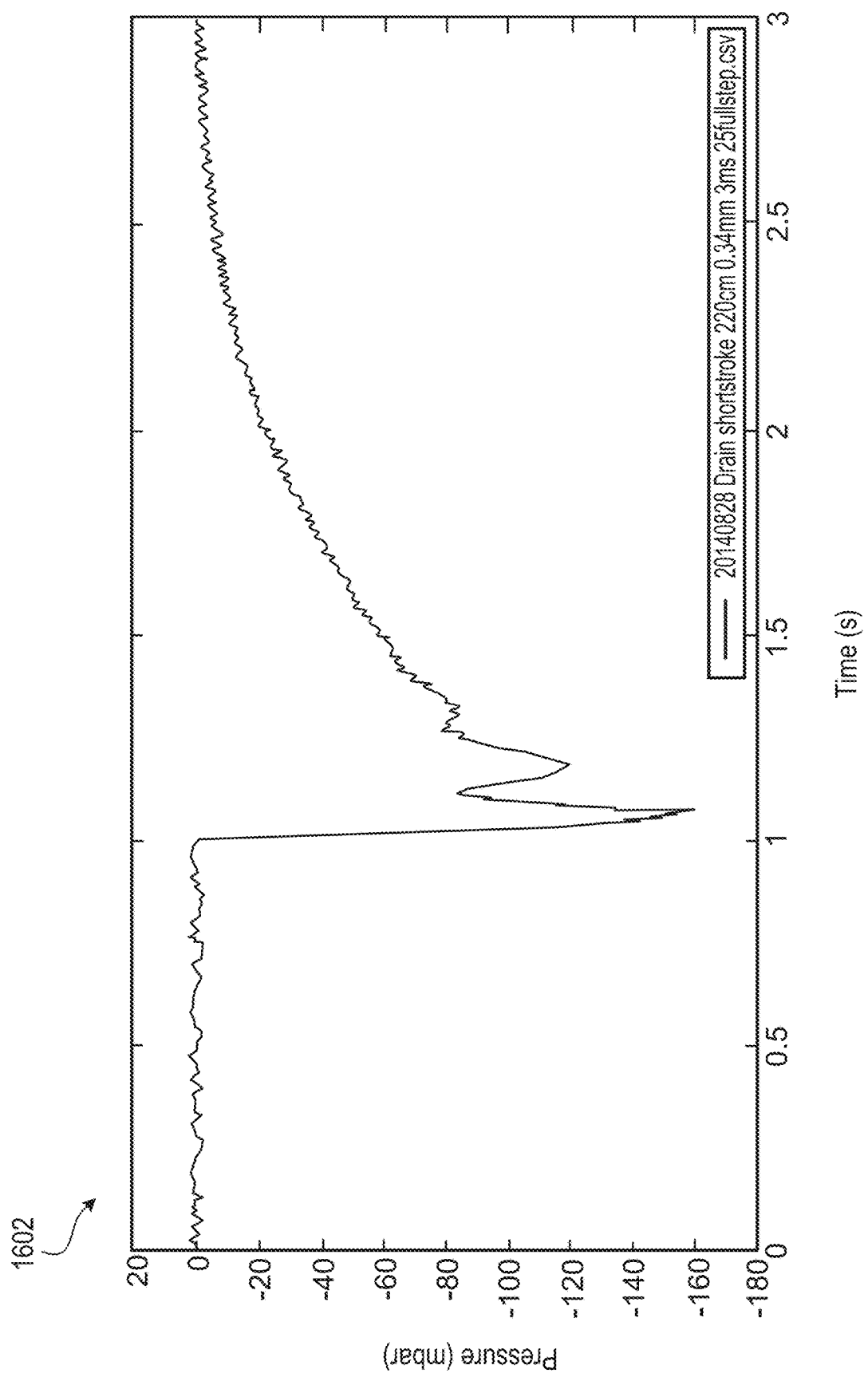
FIG. 16 shows a pressure waveform that includes pressure measurements over time made by the pressure sensor of FIG. 15.

FIG. 16 shows a pressure waveform 1602 that includes pressure measurements over time made by the pressure sensor 151A during the short-stroke test. The pressure measurements were sampled at a frequency of 1 kHz. In this example, the occlusion 1508 of drain-critical value was positioned at a distance x=220 centimeters along the patient line 1530. The measured pressure, relatively steady in the absence of pump motion, is seen to drop rapidly during a pump stroke having a duration of approximately 75 milliseconds that commences at approximately t=1 second. After abrupt cessation of pump motion, the pressure in the patient line 1530 slowly returns to its steady-state value (e.g., due to the leakage of the partial occlusion). The slope of the pressure versus time curve during the short-stroke can be evaluated to determine the fluidic capacitance $C_f$ according to Equation 8. Once the fluidic capacitance $C_f$ is known, locations x of occlusions (e.g., at unknown positions of the conduit) can then be determined by evaluating the slope of the pressure versus time curve during subsequent short-stroke tests.

The data shown in FIG. 16 correspond to the short-stroke test performed with a dispensed water volume of 0.33 cubic centimeters at a fixed rate of 4.4 milliliters per second for an occlusion 1508 positioned at a distance x=220 centimeters along the patient line 1530. Data was also obtained for various other cassette 112/occlusion 1508 configurations at various different distances x for the occlusion 1508. For each test, the slope of the pressure versus time curve during the main downward event of the short-stroke was evaluated to determine the fluidic capacitance $C_f$, and the fluidic capacitances $C_f$ were correlated to the various different distances x of the occlusions 1508. The correlated data can be used to create a calibration curve for refining future determinations of occlusion 1508 locations. In this way, errors between calculated distances x according to Equation 6 and the actual distances x of the occlusions 1508 during testing can be considered for calibrating future distance x calculations.

Experiment 3

Another way to determine the fluidic capacitance $C_f$ of a pressurized region of a conduit is to measure the amount of time required for pressure measurements to decay below a predetermined threshold after fluid is provided to or withdrawn from the conduit in a long, steady-state stroke at a known volumetric flow rate. Like Experiment 2, which studied a technique for determining the fluidic capacitance $C_f$ of a pressurized region of a conduit by measuring a change in pressure during a short dispensing or withdrawing stroke, Experiment 3 was also implemented in an actual dialysis machine (e.g., the PD machine 102 of FIGS. 1-10) using the built-in pressure sensor 151A to test for partial blockages. The test setup was substantially similar to that described above with respect to Experiment 2 and as shown in FIG. 15.

The distance x to the occlusions 1508 can be inferred from a measurement of the fluidic capacitance $C_f$ of a pressurized region of a conduit (e.g., the segment of the patient line 1530 between the PD cycler 102 and the occlusion 1508, sometimes referred to as the first portion). The occlusion 1508 may define a boundary between the first portion of the conduit and a second portion of the conduit (e.g., the rest of the conduit). For a patient line 1530 with tubing of uniform mechanical properties and cross-sectional dimensions (e.g., which is largely true in practice), the fluidic capacitance $C_f$ is related proportionately to the length of tubing comprising the "capacitor." As described above, the so-called capacitor can be "charged" by adding or withdrawing fluid. The capacitor may then be discharged by cessation of pump flow and thus passively communicating fluid to or from the patient (e.g., the patient's peritoneal cavity). The fluidic capacitance $C_f$ may be inferred from a characteristic time of the pressure decay that occurs during the discharge.

In general, a characteristic time is an estimate of the order of magnitude of the reaction time scale of a system. In the context of RC circuits and its fluidic analogy to Ohm's Law, the characteristic time is the time required for the capacitor to discharge by 1−1/e (e.g., by approximately 63.2%) from the initial value to the final (e.g., asymptotic) value. Thus, in focusing on the fluidic analogy to RC circuits explored herein, the characteristic time is the time required for the pressure inside the patient line 1530 to change from the initial pressure value to 36.8% of the difference between the initial pressure value and the final pressure value. The characteristic time can be expressed as a time constant, τ. Once the characteristic time constant r is known, the fluidic capacitance $C_f$—and in turn, distance x to the occlusion—can be determined.

Equation 6 presents the theoretical basis by which the fluidic capacitance $C_f$ is expected to be proportional to the distance x to the occlusion, with the constant of proportionality being a function only of tubing properties and cross-sectional dimensions. The relationship between the fluidic capacitance $C_f$ and the characteristic time constant r is expressed in Equation 9:

$$\tau = R_f C_f \quad (9)$$

where $R_f$ is the fluidic resistance representing the partial occlusion itself. The fluidic resistance $R_f$ may be estimated from the fluidic analogy to Ohm's Law, as shown in Equation 10:

$$R_f = \Delta P/Q \quad (10)$$

where Q is an imposed volumetric flow rate and $\Delta P$ is the change in pressure in response to the imposed volumetric flow rate Q (e.g., the pressure drop across the occlusion).

Experiment 3 included the following general steps, which were performed for occlusions at various different distances:
  i. use the pump to add (for Fill Direction testing) or withdraw (for Drain Direction testing) flow at a fixed and known volumetric flow rate Q, measuring steady-state pressure achieved during this initial flow event;
  ii. determine the fluidic resistance $R_f$ using Equation 10;
  iii. abruptly stop the flow to allow passive decay of the pressure within the conduit, measuring the pressure versus time during the decay of pressure;
  iv. determine the characteristic time constant r using the pressure measurements;
  v. calculate the fluidic capacitance $C_f$ using Equation 9; and
  vi. empirically determine a calibration curve between fluidic capacitance $C_f$ and distance x to the occlusion using Equation 6.

The experiment was performed at various distances x and across a large number of cassettes, with different types, degrees, and locations of flow restriction (e.g., occlusions), in order to investigate the potential sensitivity and specificity of the detection method.

In this example, fill direction testing will be discussed. A volume of fluid is provided to the patient line 1530 in a long, steady-state stroke at a known volumetric flow rate Q (e.g., sometimes referred to as a "long stroke"). During the pump stroke, an initial steady-state pressure $P_1$ is reached within the patient line 1530, as measured by the pressure sensor 151A. The initial steady-state pressure $P_1$ represents the pressure that results from the fixed volumetric flow rate Q and the characteristics of the occlusion 1508. The initial steady-state pressure $P_1$ is used to calculate the fluidic resistance $R_f$ using Equation 10, where $\Delta P$ is the difference between the initial pressure in the patient line 1530 (e.g., before the pump stroke begins) and the initial steady-state pressure $P_1$ achieved during the pump stroke. In some implementations, the initial steady-state pressure $P_1$ is measured right before the long stroke is stopped, or when the long stroke is stopped.

At the end of the pump stroke, the flow is abruptly stopped to allow passive decay of the pressure within the patient line 1530. The pressure sensor 151A makes pressure measurements during the decay of pressure until a final steady-state pressure $P_f$ is achieved (e.g., until the decay is complete and the pressure is not changing anymore). In some implementations, the pump stroke can be abruptly ceased as soon as it is determined that an initial steady-state pressure $P_1$ has been reached. Once the initial steady-state pressure $P_1$ and the final steady-state pressure $P_f$ are known, the characteristic time constant $\tau$ is determined. The characteristic time constant $\tau$ is an elapsed time between the occurrence of the initial steady-state pressure $P_1$ and the occurrence of one of the plurality of pressure measurements taken during the decay of pressure.

Figure 17A:
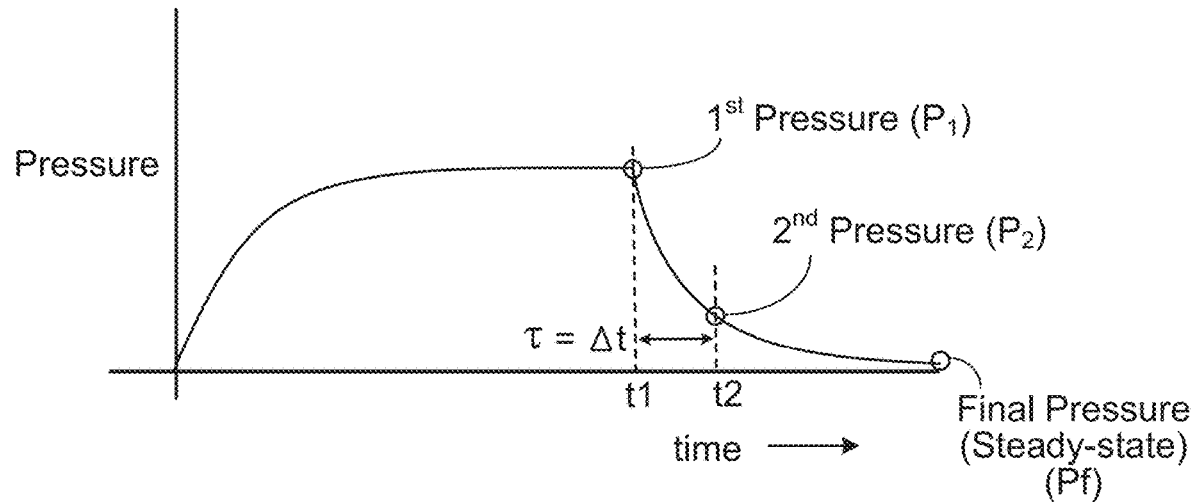
FIGS. 17A-C show examples of pressure versus time plots that illustrate how a characteristic time constant $\tau$ is determined.
Figure 17B:
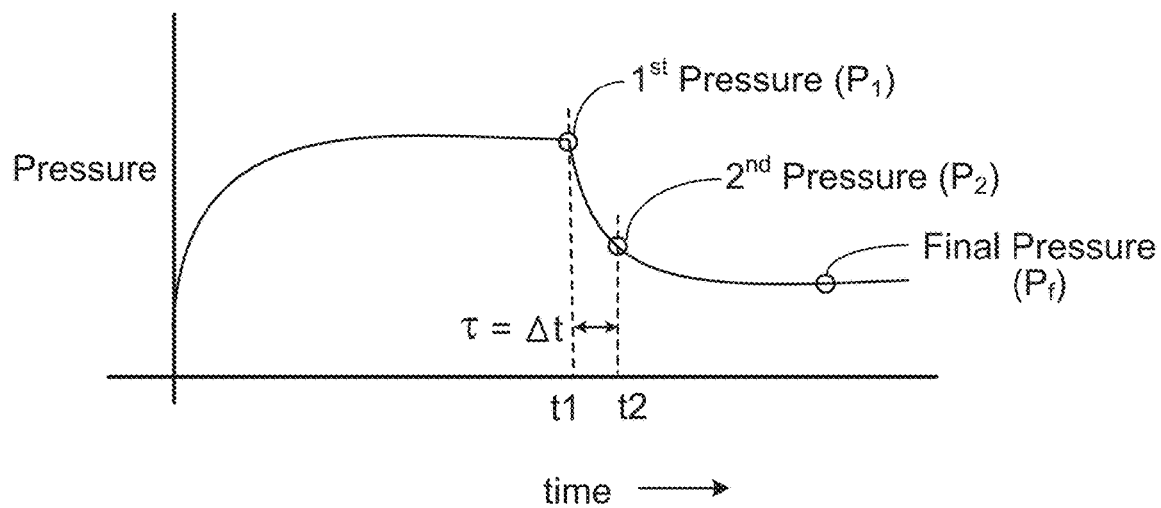
Figure 17C:
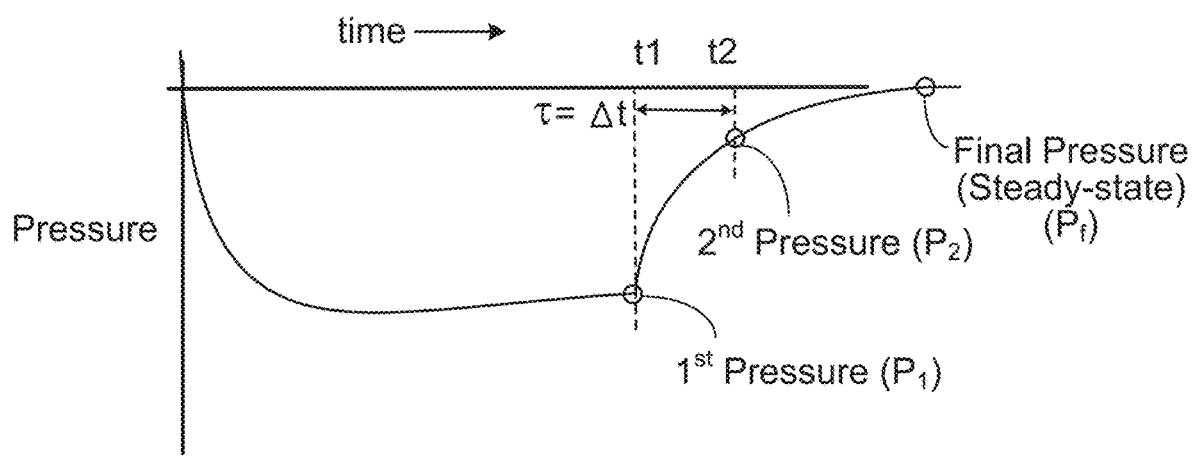

FIGS. 17A-C show examples of pressure versus time plots that illustrate how the characteristic time constant $\tau$ for a pressurized region of the patient line 1530 (e.g., acting as a capacitor) can be determined. The plot shown in FIG. 17A shows pressure measurements that are made during and after a dispensing (e.g., "fill") stroke. For example, "charging" of the capacitor occurs when fluid is provided to the patient line 1530, which corresponds to t=0 to t=$t_1$ in the plot. The pressure reaches an initial steady-state value $P_1$. At t=$t_1$, the flow is abruptly ceased and the pressure begins to decrease (e.g., the capacitor begins to discharge). The pressure eventually reaches a final steady-state value $P_f$. In this example, the final steady-state value is at or near zero. Knowing the initial $P_1$ and final $P_f$ steady-state values, the pressure $P_2$ that represents 36.8% of the difference between the initial $P_1$ and final $P_f$ steady-state values can be determined. This pressure $P_2$ has a value of $1/e*(P_1-P_f)$. The characteristic time constant $\tau$ can then be determined by identifying the time at which the pressure inside the patient line 1530 is equal to $P_2$ and determining the elapsed time between $t_1$ and $t_2$.

In some implementations, the final steady-state pressure $P_f$ may not be zero. FIG. 17B shows a plot of pressure measurements that approach a non-zero final steady-state value $P_f$. For example, the patient may be at an elevation that is different than that of the pressure sensor 151A, and thus there exists a non-zero hydrostatic pressure in the case of zero flow in the patient line 1530. In such cases, the pressure $P_2$ that represents 36.8% of the difference between the initial $P_1$ and final $P_f$ steady-state values has a value of $1/e*(P_1-P_f)+P_f$. The characteristic time constant $\tau$ can then be determined by identifying the time at which the pressure inside the patient line 1530 is equal to $P_2$ and determining the elapsed time between $t_1$ and $t_2$.

In some implementations, a time-averaged pre-stroke zero-flow value may be subtracted from the pressure measurements as an initial step before determining the characteristic time constant r. In this way, one or both of the starting pressure (e.g., at t=0) and the final steady-state pressure $P_f$ can be adjusted to have a value of 0 mbar, thereby simplifying the characteristic time constant $\tau$ determination.

A similar method can be used for determining the characteristic time constant $\tau$ when withdrawing fluid from the patient line 1530. The plot shown in FIG. 17C shows pressure measurements that are made during and after a withdrawing (e.g., "drain") stroke. For example, "charging" of the capacitor occurs when fluid is withdrawn from the patient line 1530, which corresponds to t=0 to t=$t_1$ in the plot. The pressure reaches an initial steady-state value $P_1$. At t=$t_1$, the flow is ceased and the pressure begins to increase (e.g., the capacitor begins to discharge). The pressure eventually reaches a final steady-state value $P_f$ In this example, the final steady-state value is at or near zero. Knowing the initial $P_1$ and final $P_f$ steady-state values, the pressure $P_2$ that represents 36.8% of the difference between the initial $P_1$ and final $P_f$ steady-state values can be determined. This pressure $P_2$ has a value of $1/e*(P_1-P_f)$. The characteristic time constant $\tau$ can then be determined by identifying the time at which the pressure inside the patient line 1530 is equal to $P_2$ and determining the elapsed time between $t_1$ and $t_2$. In implementations in which the final steady-state pressure $P_f$ is not zero, the characteristic time constant $\tau$ can be determined in a manner similar to that described above with respect to FIG. 17B.

Once the characteristic time constant $\tau$ is determined, the fluid capacitance $C_f$ is calculated according to Equation 9. The distance x to the occlusion 1508 is then determined according to Equation 6.

Similar tests can be performed for various other cassette 112/occlusion 1508 configurations at various different distances x for the occlusion 1508. For each test, the calculated fluidic capacitances $C_f$ can be correlated to the various different distances x of the occlusions 1508. The correlated data can be used to create a calibration curve for refining future determinations of occlusion 1508 locations. In this way, errors between calculated distances x according to Equation 6 and the actual distances x of the occlusions 1508 during testing can be considered for calibrating future distance x calculations.

Experiment 4

In some implementations, instead of or in addition to determining the exact distance x to the occlusion, the relative location and/or the general location of the occlusion may be determined. For example, characteristics of a plurality of pressure measurements within the conduit can be analyzed to determine whether the occlusion is present in a region of particular interest, such as in a patient line region (e.g., outside the patient) or a catheter region (e.g., inside the patient) of the conduit. The conduit may include a fluid capacitive element that is strategically positioned between the patient line region and the catheter region such that the generated information can localize the occlusion to one region or the other. Based on the determined region of the occlusion, the type of the occlusion (e.g., a pinch in the patient line, an occlusion of the catheter, etc.) can be determined. The determination may be made using existing components (e.g., the pressure sensor 151A) of the PD machine (102 of FIG. 1), and without requiring backward flow in the detection procedure.

Figure 18:
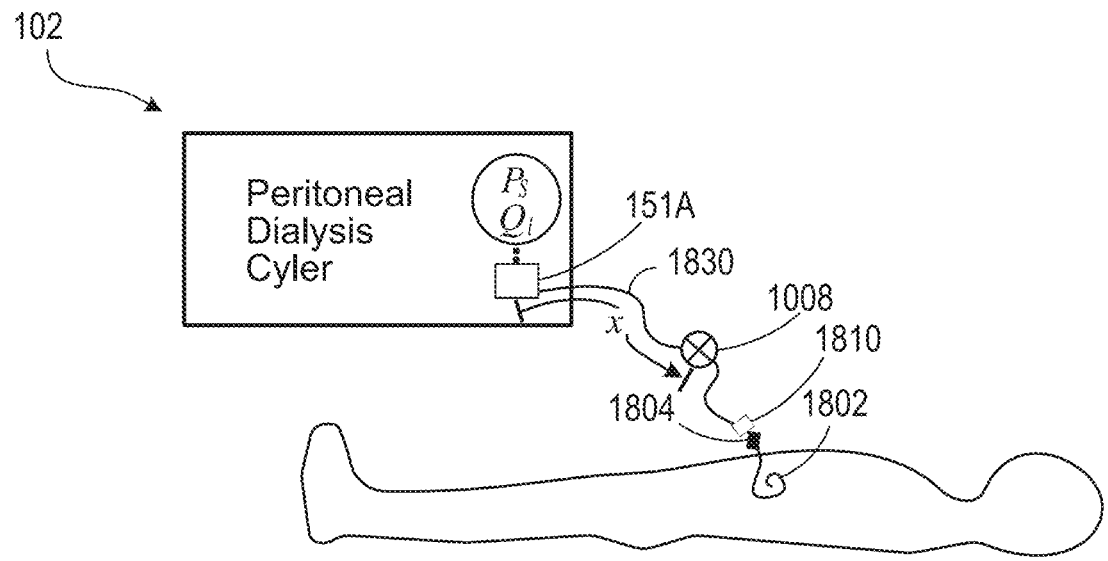
FIG. 18 shows a schematic diagram of the PD cycler of FIG. 1 connected to a patient.

FIG. 18 shows a schematic diagram of the PD machine 102 connected to a patient. A proximal end of a patient line 1830 is connected to the PD machine 102 at a port (e.g., an inlet/outlet), and a distal end of the patient line 1830 is connected to the patient's abdomen via a catheter 1802. The catheter 1002 is connected to the patient line via a port 1804. A fluid capacitive element 1810 is positioned at the distal end of the patient line 1830 adjacent the port 1804. In some examples, the fluid capacitive element 1810 may be positioned elsewhere. The patient line 1830 may be a tube made of a distensible and/or flexible material that is at least partially distended by operating pressures in the PD machine 102. For example, the patient line 1830 may be made of an elastomeric material such as a polymer that develops a swell in response to positive operating pressures in the PD machine 102. The pressure sensor 151A is configured to measure the pressure in the patient line 1830. The patient line 1830, the fluid capacitive element 1810, the port 1804, and the catheter 1802 are sometimes referred to herein as the patient line-catheter conduit, or simply the conduit. The conduit may be substantially similar to that described above with respect to FIG. 10, except in this example, the conduit also includes the fluid capacitive element 1810.

Like the patient line 1830, the fluid capacitive element 1810 may also be made of a distensible and/or flexible material that is at least partially distended by operating pressures in the PD machine 102. For example, the fluid capacitive element 1810 may be made of an elastomeric material such as a polymer that develops a swell in response to positive operating pressures in the PD machine 102. In some implementations, the fluid capacitive element 1810 may be part of the patient line 1830 (e.g., an elastomeric segment integrated into the patient line 1830). The fluid capacitive element 1810 may have a distensibility that is substantially greater than that of the patient line 1830 itself. For example, the fluid capacitive element 1810 may have the capability to store additional fluid volume with a concomitant increase in local liquid pressure produced by a restoring force. Accordingly, occlusions that occur between the patient line port of the PD machine 102 and the fluid capacitive element 1810 do not cause the pressure sensor 151A to experience the effects of the fluid capacitive element 1810, and occlusions that occur between the fluid capacitive element 1810 and the tip of the catheter 1802 do cause the pressure sensor 151A to experience the effects of the fluid capacitive element 1810.

During a PD treatment cycle, an occlusion can occur at different locations in the conduit. For example, the patient line 1830 may become kinked or pinched, holes in the catheter 1802 may become occluded (e.g., with omental fat), or the patient line 1830 may develop an internal blockage at some location (e.g., from a deposit of omental fat). The PD machine 102 is configured to adjust its operation in response to an occlusion being detected, as described above with respect to FIG. 10. An appropriate response by the PD machine 102 may depend on the type of the occlusion, and the type of the occlusion may be ascertained based on whether the occlusion occurs in the patient line region (e.g., between the patient line port and the fluid capacitive element 1810) or the catheter region (e.g., between the fluid capacitive element 1810 and the tip of the catheter 1802) of the conduit.

Figure 19:
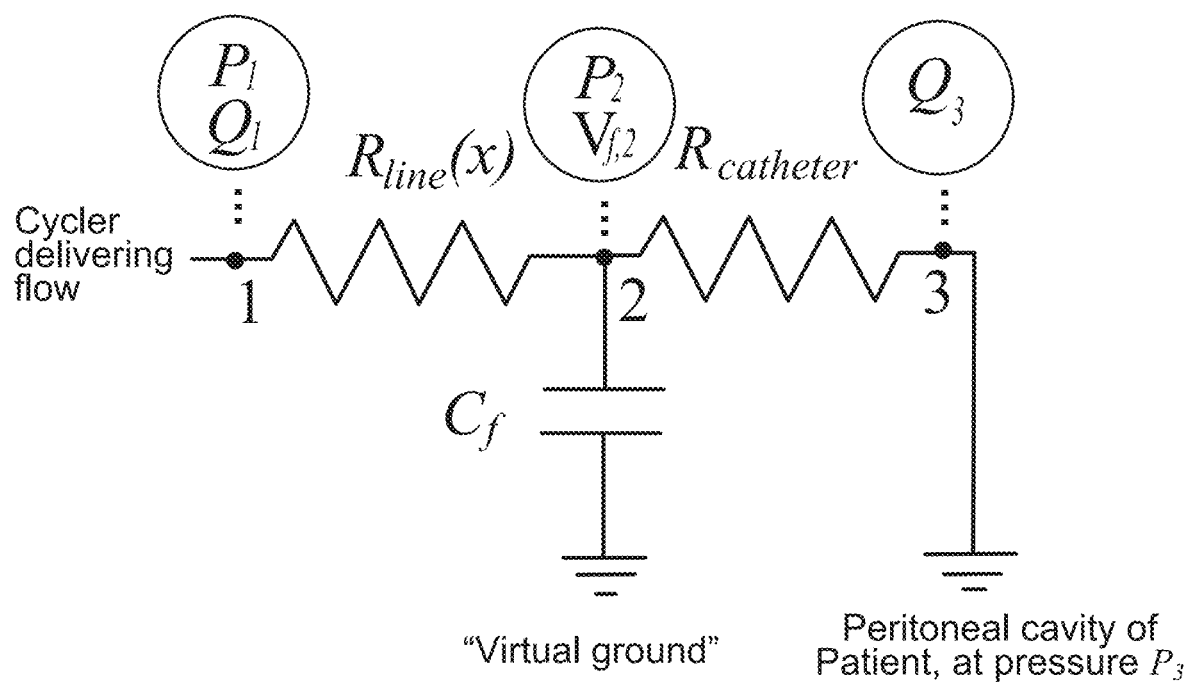
FIG. 19 shows a representation of a lumped-element electrical circuit analogous to the fluidic system of FIG. 18.

To help illustrate the method of analyzing the effect achieved by the addition of the fluid capacitive element 1810 to the conduit, FIG. 19 shows a representation of a lumped-element electrical circuit that is analogous to the fluidic system shown in FIG. 18, in which P refers to pressures at various portions of the conduit, Q refers to the volumetric flow rate at various portions of the conduit, R refers to the fluidic resistance (e.g., including a patient line fluidic resistance component Rime and a catheter fluidic resistance component $R_{catheter}$, collectively $R_f$), $V_f$ refers to the fluid volume, and $C_f$ refers to the fluid capacitance. Fluid mechanical analysis can be performed by drawing mathematical similarity to the analogous electrical circuit. A lumped element analysis can be performed in which fluid mechanical effects occurring over a distributed region of the conduit are represented by a discrete analytical elements (e.g., resistor or capacitor).

The electrical circuit analogies for the fluid mechanic lumped element analysis are shown in Table 1, and the physical and mathematical analogies consistent with the equations in Table 1 are shown in Table 2:

TABLE 1

| Circuit Element | Electrical Constitutive Law | Fluid Effect | Fluid Constitutive Law | Representative Expression for Fluid Lumped Parameter |
|---|---|---|---|---|
| Resistor | $\Delta V = IR$ | Viscous pressure loss | $\Delta P = QR_f$ | $R_f = \dfrac{8\mu l}{\pi r^4}$ |
| Capacitor | $\Delta V = \dfrac{\Delta q}{C}$ | Fluid storage with restoring force | $\Delta P = \dfrac{\Delta V_f}{C_f}$ | $C_f \equiv \dfrac{A \Delta V_f}{\Delta F}$ |
| Inductor | $\Delta V = L\dfrac{dI}{dt}$ | Fluid inertia | $\Delta P = L_f \dfrac{dQ}{dt}$ | $L_f = \dfrac{\rho l}{\pi r^2}$ |

TABLE 2

| Electrical Quantity | Analogous Fluid Quantity |
|---|---|
| Potential drop or change, $\Delta V$ | Pressure drop or change, $\Delta P$ |
| Charge, q | Fluid volume, $V_f$ |
| Current, I | Volumetric flow rate, Q |
| Resistance, R | Fluidic resistance, $R_f$ |

TABLE 2-continued

| Electrical Quantity | Analogous Fluid Quantity |
|---|---|
| Capacitance, C | Fluidic capacitance, $C_f$ |
| Inductance, L | Fluidic inductance, $L_f$ |

Various assumptions may be made to simplify the mathematical analysis of the equations of Table 1, although such assumptions may not be required in all cases. For example, it may be assumed that the capacitive effects are linear (e.g., pressure increases proportional to fluid volume stored). The fluidic resistance $R_f$ may apply to the case of fully developed laminar flow in a rigid duct of circular cross-section (e.g., constant radius r, length l); for other internal flow situations, other expressions for the fluidic resistance $R_f$ may apply. In the general case (e.g., including turbulent or separating flow), the fluidic resistance $R_f$ itself is a function of the volumetric flow rate Q. The dynamic viscosity is μ. As with the fluidic capacitance $C_f$, the analysis may be simplified by the linearity resulting from constant values of the fluidic resistance $R_f$, but such linearity is not required.

The fluidic capacitance $C_f$ is the change in stored volume $\Delta V_f$ of fluid divided by the quantity: change in restoring force $\Delta F$ divided by the area A over which the latter acts. The form of an expression for the fluidic capacitance $C_f$ incorporating material properties and dimensions may depend upon the design of the fluid capacitive element 1810 and its mechanism of restoring force (e.g., elastomeric, pneumatic, spring, etc.). The fluidic inductance Lf applies to fluid having a fluid density p in a circular duct segment of constant radius r and length l.

The circuit of FIG. 19 is shown without an inductor for the case in which inductive effects may be neglected, but inductive effects may be incorporated into the mathematical model if appropriate. The ordinary differential equation governing the circuit behavior can be written in terms of the time-varying volume of fluid stored in the fluid capacitive element 1810, $V_{f,2}(t)$, as expressed in Equation 11:

$$Q_1(t) = \frac{V_{f,2}(t)}{R_{catheter}C_f} + \frac{dV_{f,2}}{dt} \quad (11)$$

The object of Experiment 4 is to distinguish an increase in the fluidic resistance of the patient line region of the conduit $R_{line}$ from an increase in the fluidic resistance of the catheter region of the conduit $R_{catheter}$, by measuring the pressure in the patient line region $P_1$ (e.g., near the patient line port) over time. The pressure in the patient line region over time $P_1(t)$ is affected differently by the fluidic resistance $R_f$ increase depending upon the location of such an increase. The placement of the fluid capacitive element 1810 between the patient line region and the catheter region makes it possible to make such a distinction, as shown in the analysis below.

A specified flow waveform $Q_1(t)$ is provided to the patient line 1830. In this example, the flow waveform $Q_1(t)$ is known and is periodic such that it may be represented by a full Fourier transform as shown in Equation 12:

$$Q_1(t) = \frac{A_o}{2} + \sum_{n=1}^{N} A_n \cos(\omega_n t) + B_n \sin(\omega_n t) \quad (12)$$

Equation 11 can be solved by superposition assuming that the fluidic resistance $R_f$ and the fluidic capacitance $C_f$ values are constant. In some examples, if the fluidic resistance $R_f$ and the fluidic capacitance $C_f$ values are not constant but are repeatable functions of flow and volume, respectively, a different method may be used to determine the expected characteristics of the pressures P versus the flow waveform $Q_1(t)$, such as numerical or experimental analysis. The result of the superposition provides a prediction of the pressure measured at the cycler $P_1(t)$, as shown in Equation 13:

$$P_1(t) = \frac{A_o}{2}(R_{line} + R_{catheter}) + \sum_{n=1}^{N} \left\{ \left[ R_{line}A_n + \frac{\omega_o A_n - \omega_n B_n}{C_f(\omega_o^2 + \omega_n^2)} \right] \cos(\omega_n t) + \left[ R_{line}B_n + \frac{\omega_n A_n + \omega_o B_n}{C_f(\omega_o^2 + \omega_n^2)} \right] \sin(\omega_n t) \right\} \quad (13)$$

In Equation 13, the characteristic frequency of the circuit $\omega_0$ is given by Equation 14:

$$\omega_o = \frac{1}{R_{catheter}C_f} \quad (14)$$

Equation 13 expresses the pressure at the cycler $P_1(t)$ (e.g., the pressure in the patient line region of the conduit as measured by the pressure sensor 151A) as the sum of a time-averaged and a transient (e.g., fluctuating) component. The time-averaged component is a function of the total fluidic resistance $R_f$ of the conduit:

$$\bar{P}_1 = \frac{A_o}{2}(R_{line} + R_{catheter}).$$

Hence, an equivalent increase in either the fluidic resistance of the patient line region $R_{line}$ or the fluidic resistance of the catheter region $R_{catheter}$ will affect $P_1$ equally. Thus, the time-averaged value of the pressure $P_1(t)$ cannot be used to identify the location of a sudden increase in flow resistance.

On the other hand, inspection of the transient component of the pressure $P_1(t)$ reveals a separation of the effects of the fluidic resistance of the patient line region Rime versus the fluidic resistance of the catheter region $R_{catheter}$. A change in the fluidic resistance of the catheter region $R_{catheter}$ affects the characteristic frequency $\omega_0$, while a change in the fluidic resistance of the patient line region $R_{line}$ does not. Conversely, a change in the fluidic resistance of the patient line region $R_{line}$ alone affects the transient component of the pressure $P_1(t)$ through the terms $R_{line}A_n$ and $R_{line}B_n$. Thus, if the transient component of the pressure $P_1(t)$ is measured and compared to expected characteristics, the location of an increase in flow resistance may be determined.

Because the values of $A_n$ and $B_n$ depend upon the shape of $Q_1(t)$, and the latter is to be imposed by design of the pump head operational protocol, it is advantageous to determine which waveform(s) $Q_1(t)$ will most specifically and sensitively reveal the location of resistance increase. Laplace transform analysis and experimental data provide the recommendations to follow.

An ordinary differential equation (e.g., such as Equation 11) with constant coefficients and a periodic forcing function, including one of impulsive character, is a good candidate for solution by the method of Laplace transforms. The solution may proceed as follows according to Equations 15-25, and its result complements that obtained by Fourier analysis in the previous section:

$$\mathcal{L}[Q_1(t)] = \mathcal{L}\left[\frac{V_{f,2}(t)}{R_{catheter}C_f}\right] + \mathcal{L}\left(\frac{dV_{f,2}}{dt}\right) \quad (15)$$

$$\mathcal{L}[Q_1(t)] = \frac{1}{R_{catheter}C_f}\mathcal{L}[V_{f,2}(t)] + s\mathcal{L}[V_{f,2}(t)] - V_{f,2}(0) \quad (16)$$

$$\mathbb{Q}(s) = \left(\frac{1}{R_{catheter}C_f} + s\right)\mathbb{V}(s) - V_{f,2}(0) \quad (17)$$

where $\mathbb{Q}(s)$ and $\mathbb{V}(s)$ are the Laplace transforms of $Q_1(t)$ and $V_{f,2}(t)$, respectively. Thus, $$\mathbb{V}(s) = \left(\frac{1}{s + \frac{1}{R_{catheter}C_f}}\right)[\mathbb{Q}(s) + V_{f,2}(0)] \quad (18)$$

where $V_{f,2}(t)$ is found by performing the inverse Laplace transform of Equation 18:

$$\mathbb{V}(s) = V_{f,2}(0)\left(\frac{1}{s + \frac{1}{R_{catheter}C_f}}\right) + \left(\frac{1}{s + \frac{1}{R_{catheter}C_f}}\right)\mathbb{Q}(s) \quad (19)$$

$$\mathbb{V}(s) = V_{f,2}(0)\mathbb{G}(s) + \mathbb{G}(s)\mathbb{Q}(s) \quad (20)$$

where $$\mathbb{G}(s) = \frac{1}{s + \frac{1}{R_{catheter}C_f}},$$

the inverse Laplace transform of which is $g(t) = e^{-w_0 t}$ (see Equation 14).

Proceeding to invert Equation 20 according to the linearity properties of the transform and the convolution rule, $$V_{f,2} = V_{f,2}(0)g(t) + \int_0^t g(t-\tau)Q_1(\tau)d\tau \quad (21)$$

$$V_{f,2}(t) = V_{f,2}(0)e^{-\omega_0 t} + \int_0^t e^{-\omega_0(t-\tau)}Q_1(\tau)d\tau \quad (22)$$

Equation 22 provides input for Equation 24, an equation for the measured pressure $P_1(t)$, derived according to the circuit equations:

$$P_2(t) = \frac{V_{f,2}(t)}{C_f} \quad (23)$$

$$P_1(t) = P_2(t) + Q_1(t)R_{line} = \frac{V_{f,2}(t)}{C_f} + Q_1(t)R_{line} \quad (24)$$

Similarly to the Fourier result above but in a different mathematical form, Equation 24 demonstrates how the capacitive element creates a separation of the effects of a change in the fluidic resistance of the patient line region Rime versus a change in the fluidic resistance of the catheter region $R_{catheter}$.

Depending upon the form of the flow waveform $Q_1(t)$, the integral in Equation 22 may be evaluated either analytically or numerically. In some implementations, the flow may be programmed to simplify the expected pressure waveform and to isolate the measurement of response time. Because the flow waveform $Q_1(t)$ is to be imposed by programmed pump head motion in this example, it may be appropriate to investigate the most advantageous achievable flow waveform $Q_1(t)$ (e.g., a flow waveform $Q_1(t)$ that results in the greatest sensitivity and specificity). In some examples, a simplifying case of the flow waveform $Q_1(t)$ may be a quasi-square wave with a frequency that is much less than the nominal value of the characteristic frequency $\omega_0$. That is, if the flow waveform $Q_1(t)$ entails a single dispensing step, with flow abruptly stopped, a period may follow in which Equation 24 is approximated by Equation 25:

$$P_1(t) \approx \frac{V_{f,2}(0)}{C_f}e^{-\omega_0 t} \quad (25)$$

Equation 25 shows how the measured time response of the pressure $P_1$ may be used to measure the characteristic frequency $\omega_0$. Once the characteristic frequency $\omega_0$ is known, Equation 24 can be used to infer a change (e.g., or lack thereof) in the fluidic resistance of the catheter region $R_{catheter}$. If the change in the fluidic resistance of the catheter region $R_{catheter}$ equals a combined increase in the fluidic resistance of the patient line region Rime and the fluidic resistance of the catheter region $R_{catheter}$ detected by steady-state measurement, then the occlusion is likely positioned in the catheter region of the conduit (e.g., an occlusion of the catheter 1802). Conversely, if a combined increase in the fluidic resistance of the patient line region $R_{line}$ and the fluidic resistance of the catheter region $R_{catheter}$ has occurred without a change in the fluidic resistance of the catheter region $R_{catheter}$, then the occlusion is likely positioned in the patient line region of the conduit (e.g., a pinch of the patient line 1830).

In some implementations, the volumetric flow rate Q may be imposed in other ways; that is, the flow waveform $Q_1(t)$ may take on other forms. For example, in some implementations, the flow waveform $Q_1(t)$ can include a steady-state introduction of fluid, a ramped introduction of fluid, a parabolic introduction of fluid, and/or a cyclical introduction of fluid.

While the detection methods described herein have sometimes been described as being implemented in a testing environment, similar techniques can be employed for detecting occlusions in the conduit when the patient line is attached to a patient receiving a dialysis treatment (e.g., as shown in FIGS. 10 and 18). For example, a determination of: i) the distance x of the occlusion, and/or ii) whether the occlusion is located in the patient line region or the catheter region of the conduit, may be made using the detection methods described herein. The type of the occlusion can then be inferred based on the determined distance and/or location.

While the dialysis system has been largely described as being a peritoneal dialysis (PD) system, other medical treatment systems can employ the techniques described herein. Examples of other medical treatment systems include hemodialysis systems, hemofiltration systems, hemodiafiltration systems, apheresis systems, and cardiopulmonary bypass systems.

While a number of equations for determining various parameters have been described above, in some implementations, such equations are used to illustrate a theoretical basis for the systems and techniques described herein and associated measurements and/or calculations. In some implementations, one or more elements of an equation may be different than those shown above. In some implementations, one or more values may be determined by empirical evaluation. For example, as described above with respect to Equation 6, in practice the relationship between the fluidic capacitance $C_f$ and the distance x between the patient line port and the occlusion can be evaluated by empirical means.

Figure 20:
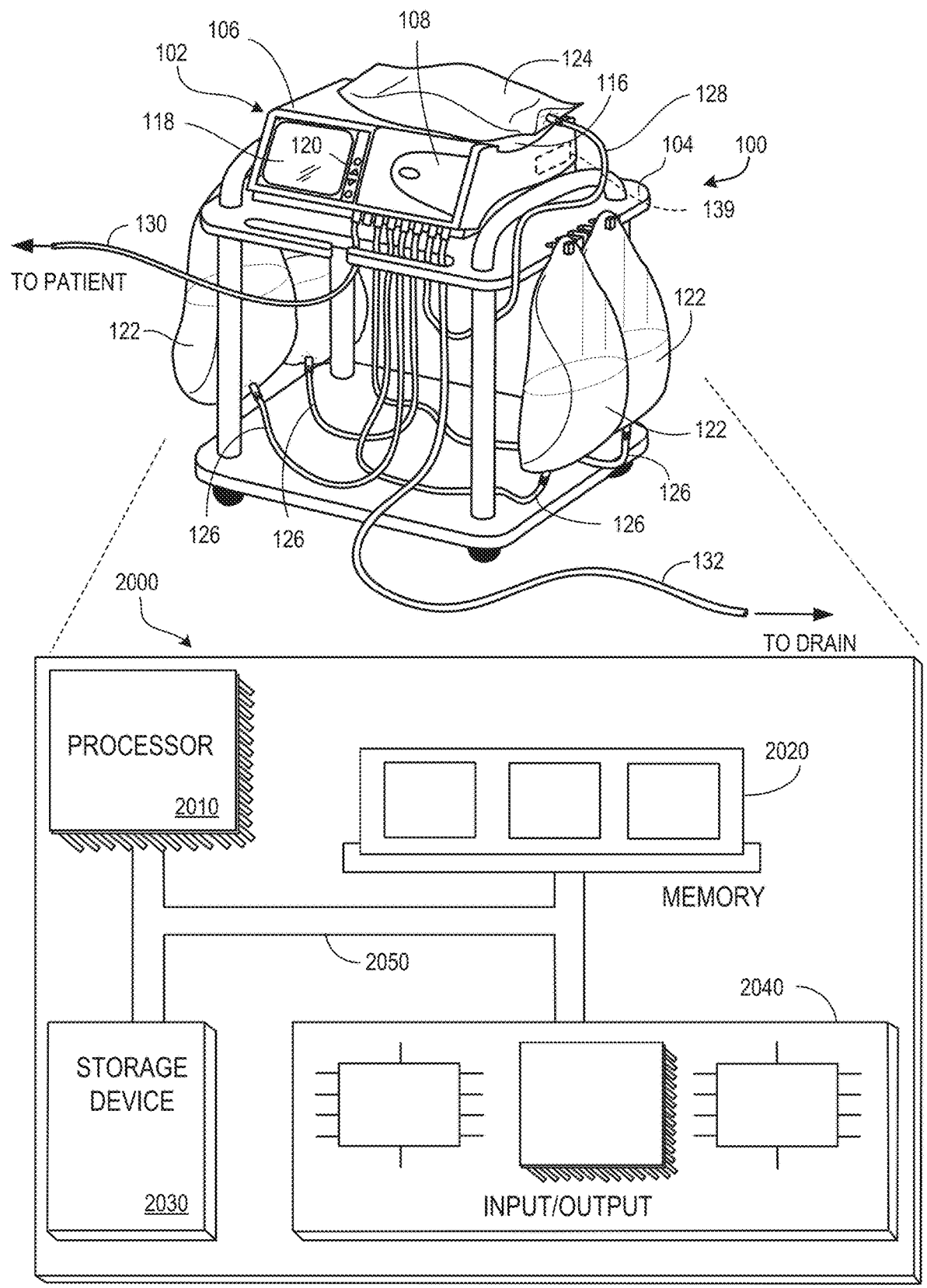
FIG. 20 shows an example of a computer system and related components.

FIG. 20 is a block diagram of an example computer system 2000. For example, the control unit (139 of FIG. 1), the computing device (1534 of FIG. 15), and/or the microcontroller (1536 of FIG. 15) could be examples of the system 2000 described here. The system 2000 includes a processor 2010, a memory 2020, a storage device 2030, and an input/output device 2040. Each of the components 2010, 2020, 2030, and 2040 can be interconnected, for example, using a system bus 2050. The processor 2010 is capable of processing instructions for execution within the system 2000. The processor 2010 can be a single-threaded processor, a multi-threaded processor, or a quantum computer. The processor 2010 is capable of processing instructions stored in the memory 2020 or on the storage device 2030. The processor 2010 may execute operations such as causing the dialysis system to carry out dialysis functions.

The memory 2020 stores information within the system 2000. In some implementations, the memory 2020 is a computer-readable medium. The memory 2020 can, for example, be a volatile memory unit or a non-volatile memory unit. In some implementations, the memory 2020 stores information for causing the pumps of the dialysis system to operate as described herein.

The storage device 2030 is capable of providing mass storage for the system 2000. In some implementations, the storage device 2030 is a non-transitory computer-readable medium. The storage device 2030 can include, for example, a hard disk device, an optical disk device, a solid-date drive, a flash drive, magnetic tape, or some other large capacity storage device. The storage device 2030 may alternatively be a cloud storage device, e.g., a logical storage device including multiple physical storage devices distributed on a network and accessed using a network.

The input/output device 2040 provides input/output operations for the system 2000. In some implementations, the input/output device 2040 includes one or more of network interface devices (e.g., an Ethernet card), a serial communication device (e.g., an RS-232 10 port), and/or a wireless interface device (e.g., an 802.11 card, a 3G wireless modem, or a 4G wireless modem). In some implementations, the input/output device 2040 may include short-range wireless transmission and receiving components, such as Wi-Fi, Bluetooth, and/or near field communication (NFC) components, among others. In some implementations, the input/output device includes driver devices configured to receive input data and send output data to other input/output devices, e.g., keyboard, printer and display devices (such as the touch screen display 118). In some implementations, mobile computing devices, mobile communication devices, and other devices are used.

In some implementations, the system 2000 is a microcontroller (e.g., the microcontroller 1536 of FIG. 15). A microcontroller is a device that contains multiple elements of a computer system in a single electronics package. For example, the single electronics package could contain the processor 2010, the memory 2020, the storage device 2030, and input/output devices 2040.

Although an example processing system has been described in FIG. 20, implementations of the subject matter and the functional operations described above can be implemented in other types of digital electronic circuitry, or in computer software, firmware, or hardware, including the structures disclosed in this specification and their structural equivalents, or in combinations of one or more of them. Implementations of the subject matter described in this specification can be implemented as one or more computer program products, i.e., one or more modules of computer program instructions encoded on a tangible program carrier, for example a computer-readable medium, for execution by, or to control the operation of, a processing system. The computer readable medium can be a machine readable storage device, a machine readable storage substrate, a memory device, a composition of matter effecting a machine readable propagated signal, or a combination of one or more of them.

The term "computer system" may encompass all apparatus, devices, and machines for processing data, including by way of example a programmable processor, a computer, or multiple processors or computers. A processing system can include, in addition to hardware, code that creates an execution environment for the computer program in question, e.g., code that constitutes processor firmware, a protocol stack, a database management system, an operating system, or a combination of one or more of them.

A computer program (also known as a program, software, software application, script, executable logic, or code) can be written in any form of programming language, including compiled or interpreted languages, or declarative or procedural languages, and it can be deployed in any form, including as a standalone program or as a module, component, subroutine, or other unit suitable for use in a computing environment. A computer program does not necessarily correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program can be deployed to be executed on one computer or on multiple computers that are located at one site or distributed across multiple sites and interconnected by a communication network.

Computer readable media suitable for storing computer program instructions and data include all forms of non-volatile or volatile memory, media and memory devices, including by way of example semiconductor memory devices, e.g., EPROM, EEPROM, and flash memory devices; magnetic disks, e.g., internal hard disks or removable disks or magnetic tapes; magneto optical disks; and CD-ROM and DVD-ROM disks. The processor and the memory can be supplemented by, or incorporated in, special purpose logic circuitry. The components of the system can be interconnected by any form or medium of digital data communication, e.g., a communication network. Examples of communication networks include a local area network ("LAN") and a wide area network ("WAN"), e.g., the Internet.

A number of implementations of the invention have been described. Nevertheless, it will be understood that various modifications may be made without departing from the spirit and scope of the invention. Accordingly, other implementations are within the scope of the following claims.

What is claimed is:
1. A method comprising:
providing or withdrawing a fluid to or from a distensible medical tube connected to a medical device at a volumetric flow rate over time, the medical tube including a patient line region and a catheter region separated by a fluid capacitive element;

measuring, by a pressure sensor at the patient line region, a plurality of pressures over time of the fluid; and determining whether an occlusion in the medical tube is present in the patient line region or the catheter region based at least partly on a fluidic resistance of the patient line region detected by a measurement of a transient component of the measured plurality of pressures over time and a fluidic resistance of the catheter region detected by the measurement of the transient component of the measured plurality of pressures over time.

2. The method of claim 1, wherein the medical device comprises a dialysis machine.

3. The method of claim 1, wherein the providing or the withdrawing the fluid to or from the distensible medical tube connected to the medical device at the volumetric flow rate comprises abruptly stopping the providing the fluid or the withdrawing the fluid.

4. The method of claim 1, wherein the providing or the withdrawing the fluid to or from the distensible medical tube connected to the medical device at the volumetric flow rate comprises one or more of a steady-state introduction of the fluid, a ramped introduction of the fluid, a parabolic introduction of the fluid, and a cyclical introduction of the fluid.

5. The method of claim 1, wherein the fluid is at least partially blocked by the occlusion.

6. The method of claim 5, wherein the fluid being at least partially blocked by the occlusion causes an increase in pressure in the medical tube or a decrease in pressure in the medical tube.

7. The method of claim 5, wherein the fluid being at least partially blocked by the occlusion causes a distension in the medical tube.

8. The method of claim 1, comprising inferring a type of the occlusion based at least in part on a determined location of the occlusion.

9. The method of claim 8, wherein the type of the occlusion comprises one or more of a pinch of the medical tube, a kink in the medical tube, a deposit in the medical tube, and a deposit blocking a hole of a catheter in the catheter region at a distal end of the medical tube.

10. The method of claim 1, wherein the determining whether the occlusion in the medical tube is present in the patient line region or the catheter region is further based on one or more of the volumetric flow rate, a second fluidic resistance of the patient line region detected by a steady-state measurement, a second fluidic resistance of the catheter region detected by the steady-state measurement, and a characteristic frequency of the transient component of the measured plurality of pressures over time.

11. A medical device comprising:
a distensible medical tube connected to a port of the medical device, the medical tube including a patient line region and a catheter region separated by a fluid capacitive element;
one or more pumps configured for providing or withdrawing a fluid to or from the medical tube at a volumetric flow rate;
a pressure sensor at the patient line region, the pressure sensor configured for measuring a plurality of pressures over time of the fluid; and
a processor configured for determining whether an occlusion in the medical tube is present in the patient line region or the catheter region based at least partly on a fluidic resistance of the patient line region detected by a measurement of a transient component of the measured plurality of pressures over time and a fluidic resistance of the catheter region detected by the measurement of the transient component of the measured plurality of pressures over time.

12. The medical device of claim 11, wherein the medical device comprises a dialysis machine.

13. The medical device of claim 12, wherein the dialysis machine comprises a peritoneal dialysis (PD) machine.

14. The medical device of claim 11, wherein the medical tube comprises a catheter in the catheter region at a distal end of the medical tube.

15. The medical device of claim 11, wherein the processor is configured to infer a type of the occlusion based at least in part on a determined location of the occlusion.

16. The medical device of claim 11, wherein the processor is configured to determine whether the occlusion in the medical tube is present in the patient line region or the catheter region further based on one or more of the volumetric flow rate, a second fluidic resistance of the patient line region detected by a steady-state measurement, a second fluidic resistance of the catheter region detected by the steady-state measurement, and a characteristic frequency of the transient component of the measured plurality of pressures over time.

17. The medical device of claim 11, wherein the fluid capacitive element is distended by pressure in the medical tube.

18. The medical device of claim 11, wherein the fluid capacitive element is integrated into the medical tube.

19. The medical device of claim 11, wherein the fluid capacitive element has a distensibility that is substantially greater than a distensibility of the medical tube.

20. The medical device of claim 11, wherein the fluid capacitive element is configured to store additional fluid volume relative to the medical tube with a concomitant increase in pressure.

* * * * *